United States Patent
Dvorak et al.

(10) Patent No.: US 11,746,135 B2
(45) Date of Patent: Sep. 5, 2023

(54) THERMOSTABLE FGF2 POLYPEPTIDE, USE THEREOF

(71) Applicants: Masarykova Univerzita, Brno (CZ); Enantis s.r.o., Brno (CZ)

(72) Inventors: Petr Dvorak, Ricmanice (CZ); Pavel Krejci, Brno-Venkov (CZ); Lukas Balek, Klimkovice (CZ); Livia Eiselleova, Mocenok (SK); Zaneta Konecna, Pardubice (CZ); Pavel Dvorak, Brno (CZ); David Bednar, Brno (CZ); Jan Brezovsky, Brno (CZ); Eva Sebestova, Tisnov (CZ); Radka Chaloupkova, Zamberk (CZ); Veronika Stepankova, Slavkov u Brna (CZ); Pavel Vanacek, Slavkov u Brna (CZ); Zbynek Prokop, Brno (CZ); Jiri Damborsky, Brno (CZ); Michaela Bosakova, Brno (CZ)

(73) Assignees: Masarykova Univerzita, Brno (CZ); Enantis s.r.o., Brno (CZ)

(*) Notice: Subject to any disclaimer, the term of this patent is extended or adjusted under 35 U.S.C. 154(b) by 1208 days.

(21) Appl. No.: 15/778,743

(22) PCT Filed: Oct. 3, 2016

(86) PCT No.: PCT/EP2016/073567
§ 371 (c)(1),
(2) Date: May 24, 2018

(87) PCT Pub. No.: WO2017/089016
PCT Pub. Date: Jun. 1, 2017

(65) Prior Publication Data
US 2020/0270320 A1 Aug. 27, 2020

(30) Foreign Application Priority Data
Nov. 27, 2015 (EP) .................................... 15196802

(51) Int. Cl.
C07K 14/50 (2006.01)
C12N 5/00 (2006.01)

(52) U.S. Cl.
CPC .......... *C07K 14/503* (2013.01); *C12N 5/0018* (2013.01); *C12N 2501/115* (2013.01)

(58) Field of Classification Search
CPC ................ C07K 14/503; C12N 5/0018; C12N 2501/115
See application file for complete search history.

(56) References Cited

U.S. PATENT DOCUMENTS

| 5,143,829 A | 9/1992 | Thompson et al. |
| 5,189,148 A | 2/1993 | Akiyama et al. |

(Continued)

FOREIGN PATENT DOCUMENTS

| EP | 0345660 A1 | 12/1989 |
| EP | 2333074 A1 | 6/2011 |

(Continued)

OTHER PUBLICATIONS

Adewumi, et al., "Characterization of human embryonic stem cell lines by the International Stem Cell Initiative," Nat Biotechnol (2007) 25:803-816.

(Continued)

*Primary Examiner* — Marcia S Noble
*Assistant Examiner* — Lauren K Van Buren
(74) *Attorney, Agent, or Firm* — Wood Herron & Evans LLP

(57) ABSTRACT

The invention provides an isolated thermostable polypeptide possessing FGF2 activity and having at least 85% sequence identity to SEQ ID NO: 2 (FGF2 wt) or a functional fragment thereof, and comprising at least one amino acid substitution R31L and the use thereof in the cell biology research, regenerative medicine and related medical appli- (Continued)

```
Met Ala Ala Gly Ser Ile Thr Thr Leu Pro Ala Leu Pro Glu Asp Gly
1               5                   10                  15
Gly Ser Gly Ala Phe Pro Pro Gly His Phe Lys Asp Pro Lys Arg Leu
                20                  25                  30
Tyr Cys Lys Asn Gly Gly Phe Phe Leu Arg Ile His Pro Asp Gly Arg
            35                  40                  45
Val Asp Gly Val Arg Glu Lys Ser Asp Pro His Ile Lys Leu Gln Leu
        50                  55                  60
Gln Ala Glu Glu Arg Gly Val Val Ser Ile Lys Gly Val Cys Ala Asn
65                  70                  75                  80
Arg Tyr Leu Ala Met Lys Glu Asp Gly Arg Leu Leu Ala Ser Lys Cys
                85                  90                  95
Val Thr Asp Glu Cys Phe Phe Phe Glu Arg Leu Glu Ser Asn Asn Tyr
                100                 105                 110
Asn Thr Tyr Arg Ser Arg Lys Tyr Thr Ser Trp Tyr Val Ala Leu Lys
                115                 120                 125
Arg Thr Gly Gln Tyr  Lys Leu Gly Ser Lys Thr Gly Pro Gly Gln Lys
                130                 135                 140
Ala Ile Leu Phe Leu Pro Met Ser Ala Lys Ser
145                 150                 155
``` cations or cosmetics. Further it discloses a culture medium comprising subjected FGF2 suitable for culturing a human pluripotent stem cells involving both human embryonic stem cells and induced pluripotent stem cells.

17 Claims, 13 Drawing Sheets

Specification includes a Sequence Listing.

(56) References Cited

U.S. PATENT DOCUMENTS

| | | | |
|---|---|---|---|
| 5,202,311 | A | 4/1993 | Folkman et al. |
| 6,083,706 | A | 7/2000 | Florkiewicz et al. |
| 7,754,686 | B2 | 7/2010 | Hageman et al. |
| 8,119,776 | B1 | 2/2012 | Blaber et al. |
| 8,461,111 | B2 | 6/2013 | Blaber et al. |
| 8,481,308 | B2 | 7/2013 | Stern et al. |
| 2007/0212332 | A1 | 9/2007 | Baylink et al. |
| 2008/0038287 | A1 | 2/2008 | Meinke et al. |
| 2010/0221232 | A1 | 9/2010 | Lau et al. |
| 2012/0225479 | A1 | 9/2012 | Jeong |
| 2013/0157359 | A1 | 6/2013 | Chen et al. |
| 2013/0236959 | A1 | 9/2013 | Chen et al. |

FOREIGN PATENT DOCUMENTS

| | | |
|---|---|---|
| EP | 2930181 A1 | 10/2015 |
| WO | 9508630 A1 | 3/1995 |
| WO | 2004069298 A1 | 8/2004 |
| WO | 2012158244 A2 | 11/2012 |
| WO | 2013082196 A1 | 6/2013 |
| WO | 2013090919 A1 | 6/2013 |
| WO | 2013184962 A1 | 12/2013 |

OTHER PUBLICATIONS

Altschul, S. F. et al., "Gapped BLAST and PSI-BLAST: a new generation of protein database search programs," Nucleic Acids Res. (1997) 25:3389-3402.

Berman, H. M. et al., "The Protein Data Bank," Nucleic Acids Res. (2000) 28(1):235-242.

Buchtova, M. et al., "Instability restricts signaling of multiple fibroblast growth factors," Cell. Mol. Life Sci. (2015) 72 (12):2445-2459.

Dubey, V. K. et al., "Spackling the Crack: Stabilizign Human Fibroblast Growth Factor-1 by Targeting the N and C terminus β-Strand Interactions," J. Mol. Biol. (2007) 371:256-268.

Dvorak, P. et al., "Expression and Potential Role of Fibroblast Growth Factor 2 and Its Receptors in Human Embryonic Stem Cells," Stem Cells (2005) 23:1200-1211.

Edgar, R. C., "MUSCLE: a multiple sequence alignment method with reduced time and space complexity," BMC Bioinformatics (2004) 5:113.

Eisellova, et al., "A Complex Role for FGF-2 in Self-Renewal, Survival, and Adhesion of Human Embryonic Stem Cells," Stem Cells (2009) 27:1847-1857.

Frickey, T. et al., "CLANS: a Java application for visualizaing protein families based on pairwise similarity," Bioinformatics (2004) 20:3702-3704.

Greber, B. et al., "Fibroblast Growth Factor 2 Modulates Transforming Growth Factor β Signaling in Mouse Embryonic Fibroblasts and Human ESCs (hESCs) to Support hESC Self-Renewal," Stem Cells (2007) 25:455-464.

International Search Report in International Patent Application No. PCT/EP2016/073567, dated Dec. 19, 2016, 4 pgs.

Krejci, P. et al., "Simple, mammalian cell-based assay for identification of inhibitors of the Erk MAP kinase pathway," Invest New Drugs (2007) 25:391-395.

Kruta, M. et al., "Mutation Frequency Dynamics in HPRT Locus in Culture-Adapted Human Embryonic Stem Cells and INduced Pluripotent Stem Cells Correspond to Their Differentiated Counterparts," Stem Cells and Development (2014) 23(20):2443-2454.

Li, W. et al., "Cd-hit: a fast program for clustering and comparing large sets of protein or nucleotide sequences," Bioinformatics (2006) 22:1658-1659.

Written Opinion in International Patent Application No. PCT/EP2016/073567, dated Dec. 19, 2016, 7 pgs.

Zakrzewska, M. et al., "Highly Stable Mutants of Human Fibroblast Growth Factor-1 Exhibit Prolonged Biological Action," J. Mol. Biol. (2005) 352:860-875.

Chatzou, M. et al., Multiple Sequence Alignment Modeling: Methods and Applications, Brief Bioinform. 17: 1009-1023.

Chowdhury, B., and Garai, G., 2017, A Review on Multiple Sequence Alignment from the Perspective of Genetic Algorithm, Genomics 109: 419-431.

Koonin, E.V., and Galperin, M.Y., 2003, Sequence—Evolution—Function: Computational Approaches in Comparative Genomics. Boston: Kluwer Academic; Chapter 2, Evolutionary Concept in Genetics and Genomics.

Muntoni, A.P. et al., 2020, Aligning biological sequences by exploiting residue conservation and coevolution, Phys Rev E. 102(6-1): 062409.

Petsko, G.A., and Ringe, D., 2004, Protein Structure and Function. New Science Press Ltd, Chapter 4, From Sequence to Function: Case Studies in Structural and Functional Genomics, pp. 132-133.

Phuong, T.M. et al. 2006, Multiple alignment of protein sequences with repeats and rearrangements, Nucleic Acids Res. 34: 5932-5942.

Met Ala Ala Gly Ser Ile Thr Thr Leu Pro Ala Leu Pro Glu Asp Gly
1               5                   10                  15
Gly Ser Gly Ala Phe Pro Pro Gly His Phe Lys Asp Pro Lys Arg Leu
            20                  25                  30
Tyr Cys Lys Asn Gly Gly Phe Phe Leu Arg Ile His Pro Asp Gly Arg
        35                  40                  45
Val Asp Gly Val Arg Glu Lys Ser Asp Pro His Ile Lys Leu Gln Leu
    50                  55                  60
Gln Ala Glu Glu Arg Gly Val Val Ser Ile Lys Gly Val Cys Ala Asn
65                  70                  75                  80
Arg Tyr Leu Ala Met Lys Glu Asp Gly Arg Leu Leu Ala Ser Lys Cys
                85                  90                  95
Val Thr Asp Glu Cys Phe Phe Phe Glu Arg Leu Glu Ser Asn Asn Tyr
            100                 105                 110
Asn Thr Tyr Arg Ser Arg Lys Tyr Thr Ser Trp Tyr Val Ala Leu Lys
        115                 120                 125
Arg Thr Gly Gln Tyr   Lys Leu Gly Ser Lys Thr Gly Pro Gly Gln Lys
        130                 135                 140
Ala Ile Leu Phe Leu Pro Met Ser Ala Lys Ser
145                 150                 155

FIG. 1

1 atgggcagca gccatcatca tcatcatcac agcagcggcc tggtgccgcg cggcagccat
61 ATGgcagccg ggagcatcac cacgctgccc gccttgcccg aggatggcgg cagcggcgcc
121 ttcccgcccg gccacttcaa ggaccccaag cggctgtact gcaaaaacgg gggcttcttc
181 ctgcgcatcc accccgacgg ccgagttgac ggggtccggg agaagagcga ccctcacatc
241 aagctacaac ttcaagcaga agagagagga gttgtgtcta tcaaggagt gtgtgctaac
301 cgttacctgg ctatgaagga agatggaaga ttactggctt ctaaatgtgt tacggatgag
361 tgtttctttt ttgaacgatt ggaatctaat aactacaata cttaccggtc aaggaaatac
421 accagttggt atgtggcact gaaacgaact gggcagtata aacttggatc caaaacagga
481 cctgggcaga aagctatact ttttcttcca atgtctgcta agagcTAGct cgag

FIG. 2

SEQUENCE LISTING

```
<160> NUMBER OF SEQ ID NOS: 38

<210> SEQ ID NO 1
<211> LENGTH: 468
<212> TYPE: DNA
<213> ORGANISM: Homo sapiens

<400> SEQUENCE: 1
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
```

```
cctgggcaga aagctatact ttttcttcca atgtctgcta agagctag            468
```

<210> SEQ ID NO 2
<211> LENGTH: 155
<212> TYPE: PRT
<213> ORGANISM: Homo sapiens

<400> SEQUENCE: 2

```
Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
             20                  25                  30

Tyr Cys Lys Asn Gly Gly Phe Phe Leu Arg Ile His Pro Asp Gly Arg
         35                  40                  45

Val Asp Gly Val Arg Glu Lys Ser Asp Pro His Ile Lys Leu Gln Leu
     50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 3
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:4

<400> SEQUENCE: 3

```
atggcagccg ggagcatcac cacgctgccc gccttgcccg aggatggcgg cagcggcgcc    60
ttcccgcccg gccacttcaa ggaccccaag tggctgtact gcaaaaacgg gggcttcttc   120
ctgcgcatcc accccgacgg ccgagttgac ggggtccggg agaagagcga ccctcacatc   180
aagctacaac ttcaagcaga agagagagga gttgtgtcta tcaaaggagt gtgtgctaac   240
cgttacctgg ctatgaagga agatggaaga ttactggctt ctaaatgtgt tacggatgag   300
tgtttctttt ttgaacgatt ggaatctaat aactacaata cttaccggtc aaggaaatac   360
accagttggt atgtggcact gaaacgaact gggcagtata aacttggatc caaaacagga   420
cctgggcaga aagctatact ttttcttcca atgtctgcta agagctag               468
```

<210> SEQ ID NO 4
<211> LENGTH: 155
<212> TYPE: PRT
<213> ORGANISM: Artificial Sequence
<220> FEATURE:
<223> OTHER INFORMATION: Amino acid sequence of FGF-2 R31W

<400> SEQUENCE: 4

```
Met Ala Ala Gly Ser Ile Thr Thr Leu Pro Ala Leu Pro Glu Asp Gly
```

```
                1               5                  10                 15
            Gly Ser Gly Ala Phe Pro Pro Gly His Phe Lys Asp Pro Lys Trp Leu
                            20                  25                  30

Tyr Cys Lys Asn Gly Gly Phe Phe Leu Arg Ile His Pro Asp Gly Arg
                        35                  40                  45

Val Asp Gly Val Arg Glu Lys Ser Asp Pro His Ile Lys Leu Gln Leu
                    50                  55                  60

Gln Ala Glu Glu Arg Gly Val Val Ser Ile Lys Gly Val Cys Ala Asn
            65                  70                  75                  80

Arg Tyr Leu Ala Met Lys Glu Asp Gly Arg Leu Leu Ala Ser Lys Cys
                            85                  90                  95

Val Thr Asp Glu Cys Phe Phe Phe Glu Arg Leu Glu Ser Asn Asn Tyr
                        100                 105                 110

Asn Thr Tyr Arg Ser Arg Lys Tyr Thr Ser Trp Tyr Val Ala Leu Lys
                    115                 120                 125

Arg Thr Gly Gln Tyr Lys Leu Gly Ser Lys Thr Gly Pro Gly Gln Lys
                130                 135                 140

Ala Ile Leu Phe Leu Pro Met Ser Ala Lys Ser
            145                 150                 155

<210> SEQ ID NO 5
            <211> LENGTH: 468
            <212> TYPE: DNA
            <213> ORGANISM: Artificial Sequence
            <220> FEATURE:
            <223> OTHER INFORMATION: Nucleic acid sequence encoding the amino acid
                  sequence shown for SEQ ID NO:6

<400> SEQUENCE: 5
atggcagccg ggagcatcac cacgctgccc gccttgcccg aggatggcgg cagcggcgcc      60
ttcccgcccg gccacttcaa ggaccccaag ctgctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaggagt gtgtgctaac      240 cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact tttctttcca atgtctgcta agagctag               468

<210> SEQ ID NO 6
            <211> LENGTH: 155
            <212> TYPE: PRT
            <213> ORGANISM: Artificial Sequence
            <220> FEATURE:
            <223> OTHER INFORMATION: Aminoacid sequence of FGF-2 R31L

<400> SEQUENCE: 6

Met Ala Ala Gly Ser Ile Thr Thr Leu Pro Ala Leu Pro Glu Asp Gly
            1               5                   10                  15

Gly Ser Gly Ala Phe Pro Pro Gly His Phe Lys Asp Pro Lys Leu Leu
                            20                  25                  30

Tyr Cys Lys Asn Gly Gly Phe Phe Leu Arg Ile His Pro Asp Gly Arg
                        35                  40                  45

Val Asp Gly Val Arg Glu Lys Ser Asp Pro His Ile Lys Leu Gln Leu
                    50                  55                  60

Gln Ala Glu Glu Arg Gly Val Val Ser Ile Lys Gly Val Cys Ala Asn
```

Arg Tyr Leu Ala Met Lys Glu Asp Gly Arg Leu Leu Ala Ser Lys Cys
                85                  90                  95

Val Thr Asp Glu Cys Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 7
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:8

<400> SEQUENCE: 7
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
ctgcgcatcc accccgacgg ccgagttgac gggacccggg agaagagcga ccctcacatc   180
aagctacaac ttcaagcaga agagagagga gttgtgtcta tcaaggagt gtgtgctaac    240 cgttacctgg ctatgaagga agtggaaga ttactggctt ctaaatgtgt tacggatgag    300
tgtttctttt ttgaacgatt ggaatctaat aactacaata cttaccggtc aaggaaatac   360
accagttggt atgtggcact gaaacgaact gggcagtata aacttggatc caaaacagga   420
cctgggcaga aagctatact ttttcttcca atgtctgcta agagctag                468

<210> SEQ ID NO 8
<211> LENGTH: 155
<212> TYPE: PRT
<213> ORGANISM: Artificial Sequence
<220> FEATURE:
<223> OTHER INFORMATION: Amino acid sequence of FGF-2 V52T

<400> SEQUENCE: 8

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Thr Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys

Ala Ile Leu Phe Leu Pro Met Ser Ala Lys Ser
145                 150                 155

<210> SEQ ID NO 9
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:10

<400> SEQUENCE: 9
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctttcatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300 tgtttcttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctag                  468

<210> SEQ ID NO 10
<211> LENGTH: 155
<212> TYPE: PRT
<213> ORGANISM: Artificial Sequence
<220> FEATURE:
<223> OTHER INFORMATION: Amino acid sequence of FGF-2 H59F

<400> SEQUENCE: 10

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro Phe Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 11
<211> LENGTH: 468
<212> TYPE: DNA
<213> ORGANISM: Artificial Sequence
<220> FEATURE:
<223> OTHER INFORMATION: Nucleic acid sequence encoding the amino acid sequence shown for SEQ ID NO:12

<400> SEQUENCE: 11

```
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
ctgcgcatcc accccgacgg ccgagttgac ggggtccggg agaagagcga ccctcacatc   180
aagctacaac ttcaagcaga agagagagga gttgtgtcta tcaaaggagt gtgtgctaac   240
cgttacctgg ctatgaagga agatggaaga ttatatgctt ctaaatgtgt tacggatgag   300
tgtttctttt ttgaacgatt ggaatctaat aactacaata cttaccggtc aaggaaatac   360
accagttggt atgtggcact gaaacgaact gggcagtata aacttggatc caaaacagga   420
cctgggcaga aagctatact ttttcttcca atgtctgcta agagctag                468
```

<210> SEQ ID NO 12
<211> LENGTH: 155
<212> TYPE: PRT
<213> ORGANISM: Artificial Sequence
<220> FEATURE:
<223> OTHER INFORMATION: Amino acid sequence of FGF-2 L92Y

<400> SEQUENCE: 12

```
Met Ala Ala Gly Ser Ile Thr Thr Leu Pro Ala Leu Pro Glu Asp Gly
1               5                   10                  15
Gly Ser Gly Ala Phe Pro Pro Gly His Phe Lys Asp Pro Lys Arg Leu
            20                  25                  30
Tyr Cys Lys Asn Gly Gly Phe Phe Leu Arg Ile His Pro Asp Gly Arg
        35                  40                  45
Val Asp Gly Val Arg Glu Lys Ser Asp Pro His Ile Lys Leu Gln Leu
    50                  55                  60
Gln Ala Glu Glu Arg Gly Val Val Ser Ile Lys Gly Val Cys Ala Asn
65                  70                  75                  80
Arg Tyr Leu Ala Met Lys Glu Asp Gly Arg Leu Tyr Ala Ser Lys Cys
                85                  90                  95
Val Thr Asp Glu Cys Phe Phe Phe Glu Arg Leu Glu Ser Asn Asn Tyr
            100                 105                 110
Asn Thr Tyr Arg Ser Arg Lys Tyr Thr Ser Trp Tyr Val Ala Leu Lys
        115                 120                 125
Arg Thr Gly Gln Tyr Lys Leu Gly Ser Lys Thr Gly Pro Gly Gln Lys
    130                 135                 140
Ala Ile Leu Phe Leu Pro Met Ser Ala Lys Ser
145                 150                 155
```

<210> SEQ ID NO 13
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:14

<400> SEQUENCE: 13

```
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
ctgcgcatcc accccgacgg ccgagttgac ggggtccggg agaagagcga ccctcacatc   180
aagctacaac ttcaagcaga agagagagga gttgtgtcta tcaaaggagt gtgtgctaac   240
```

```
cgttacctgg ctatgaagga agatggaaga ttactggctt ctaaatatgt tacggatgag      300
tgtttctttt ttgaacgatt ggaatctaat aactacaata cttaccggtc aaggaaatac      360
accagttggt atgtggcact gaaacgaact gggcagtata aacttggatc caaaacagga      420
cctgggcaga aagctatact ttttcttcca atgtctgcta agagctag                   468
```

<210> SEQ ID NO 14
<211> LENGTH: 155
<212> TYPE: PRT
<213> ORGANISM: Artificial Sequence
<220> FEATURE:
<223> OTHER INFORMATION: Amino acid sequence of FGF-2 C96Y

<400> SEQUENCE: 14

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Tyr
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 15
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:16

<400> SEQUENCE: 15

```
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc      120
ctgcgcatcc accccgacgg ccgagttgac ggggtccggg agaagagcga ccctcacatc      180
aagctacaac ttcaagcaga agagagagga gttgtgtcta tcaaaggagt gtgtgctaac      240
cgttacctgg ctatgaagga agatggaaga ttactggctt ctaaatgtgt tacggatgag      300
tgtttctttt ttgaacgatt ggaagaaaat aactacaata cttaccggtc aaggaaatac      360
accagttggt atgtggcact gaaacgaact gggcagtata aacttggatc caaaacagga      420
cctgggcaga aagctatact ttttcttcca atgtctgcta agagctag                   468
```

<210> SEQ ID NO 16
<211> LENGTH: 155
<212> TYPE: PRT

<213> ORGANISM: Artificial Sequence
<220> FEATURE:
<223> OTHER INFORMATION: Amino acid sequence of FGF-2 S109E

<400> SEQUENCE: 16

```
Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Glu Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155
```

<210> SEQ ID NO 17
<211> LENGTH: 468
<212> TYPE: DNA
<213> ORGANISM: Artificial Sequence
<220> FEATURE:
<223> OTHER INFORMATION: Nucleic acid sequence encoding the amino acid sequence shown for SEQ ID NO:18

<400> SEQUENCE: 17

```
atggcagccg ggagcatcac cacgctgccc gccttgcccg aggatggcgg cagcggcgcc    60
ttcccgcccg gccacttcaa ggaccccatc cggctgtact gcaaaaacgg ggcttcttc    120
ctgcgcatcc accccgacgg ccgagttgac ggggtccggg agaagagcga ccctcacatc    180
aagctacaac ttcaagcaga agagagagga gttgtgtcta tcaaaggagt gtgtgctaac    240
cgttacctgg ctatgaagga agatggaaga ttactggctt ctaaatgtgt tacggatgag    300
tgttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctag               468
```

<210> SEQ ID NO 18
<211> LENGTH: 155
<212> TYPE: PRT
<213> ORGANISM: Artificial Sequence
<220> FEATURE:
<223> OTHER INFORMATION: Amino acid sequence of FGF-2 K30I

<400> SEQUENCE: 18

```
Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Ile Arg Leu
            20                  25                  30
```

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155

<210> SEQ ID NO 19
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:20

<400> SEQUENCE: 19
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
ctgcgcatcc accccgacgg ccgagttgac ggggtccggg acaagagcga ccctcacatc   180
aagctacaac ttcaagcaga agagagagga gttgtgtcta tcaaggagt gtgtgctaac    240 cgttacctgg ctatgaagga agatggaaga ttactggctt ctaaatgtgt tacggatgag   300
tgtttctttt ttgaacgatt ggaatctaat aactacaata cttaccggtc aaggaaatac   360
accagttggt atgtggcact gaaacgaact gggcagtata acttggatc caaaacagga   420 cctgggcaga aagctatact ttttcttcca atgtctgcta agagctag              468

<210> SEQ ID NO 20
<211> LENGTH: 155
<212> TYPE: PRT
<213> ORGANISM: Artificial Sequence
<220> FEATURE:
<223> OTHER INFORMATION: Amino acid sequence of FGF-2 E54D

<400> SEQUENCE: 20

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
             20                  25                  30

Tyr Cys Lys Asn Gly Gly Phe Phe Leu Arg Ile His Pro Asp Gly Arg
            35                  40                  45

Val Asp Gly Val Arg Asp Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

```
Val Thr Asp Glu Cys Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 21
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:22

<400> SEQUENCE: 21

```
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaggagt gtgtgctaac     240 cgttacctgg ctatgaagga agatggaaga ttactggcta tcaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga agctatact ttttcttcca atgtctgcta agagctag                 468
```

<210> SEQ ID NO 22
<211> LENGTH: 155
<212> TYPE: PRT
<213> ORGANISM: Artificial Sequence
<220> FEATURE:
<223> OTHER INFORMATION: Amino acid sequence of FGF-2 S94I

<400> SEQUENCE: 22

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ile Lys Cys
                85                  90                  95

Val Thr Asp Glu Cys Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 23
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:24

<400> SEQUENCE: 23

```
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaggagt gtgtgctaac      240 cgttacctgg ctatgaagga agatggaaga ttactggctt ctaaaaacgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctag                  468
```

<210> SEQ ID NO 24
<211> LENGTH: 155
<212> TYPE: PRT
<213> ORGANISM: Artificial Sequence
<220> FEATURE:
<223> OTHER INFORMATION: Amino acid sequence of FGF-2 C96N

<400> SEQUENCE: 24

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Asn
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 25
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:26

<400> SEQUENCE: 25

```
atggcagccg ggagcatcac cacgctgccc gccttgcccg aggatggcgg cagcggcgcc      60
```

```
ttcccgcccg gccacttcaa ggaccccaag cggctgtact gcaaaaacgg gggcttcttc      120
ctgcgcatcc accccgacgg ccgagttgac ggggtccggg agaagagcga ccctcacatc      180
aagctacaac ttcaagcaga agagagagga gttgtgtcta tcaaaggagt gtgtgctaac      240
cgttacctgg ctatgaagga agatggaaga ttactggctt ctaaatgtgt tacggatgag      300
tgtttctttt ttgaacgatt gcactctaat aactacaata cttaccggtc aaggaaatac      360
accagttggt atgtggcact gaaacgaact gggcagtata aacttggatc aaaacagga      420 cctgggcaga aagctatact ttttcttcca atgtctgcta agagctag                   468
```

<210> SEQ ID NO 26
<211> LENGTH: 155
<212> TYPE: PRT
<213> ORGANISM: Artificial Sequence
<220> FEATURE:
<223> OTHER INFORMATION: Amino acid sequence of FGF-2 E108H

<400> SEQUENCE: 26

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu His Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 27
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:28

<400> SEQUENCE: 27

```
atggcagccg ggagcatcac cacgctgccc gccttgcccg aggatggcgg cagcggcgcc       60
ttcccgcccg gccacttcaa ggaccccaag cggctgtact gcaaaaacgg gggcttcttc      120
ctgcgcatcc accccgacgg ccgagttgac ggggtccggg agaagagcga ccctcacatc      180
aagctacaac ttcaagcaga agagagagga gttgtgtcta tcaaaggagt gtgtgctaac      240
cgttacctgg ctatgaagga agatggaaga ttactggctt ctaaatgtgt tacggatgag      300
tgtttctttt ttgaacgatt ggaatctaat aactacaata cttaccggtc aaggaaatac      360
cccagttggt atgtggcact gaaacgaact gggcagtata aacttggatc aaaacagga      420
```
cctgggcaga aagctatact ttttcttcca atgtctgcta agagctag        468

<210> SEQ ID NO 28
<211> LENGTH: 155
<212> TYPE: PRT
<213> ORGANISM: Artificial Sequence
<220> FEATURE:
<223> OTHER INFORMATION: Amino acid sequence of FGF-2 T121P

<400> SEQUENCE: 28

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Pro Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 29
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:30

<400> SEQUENCE: 29
atggcagccg ggagcatcac cacgctgccc gccttgcccg aggatggcgg cagcggcgcc        60
ttcccgcccg gccacttcaa ggaccccaag ctgctgtact gcaaaaacgg gggcttcttc       120
ctgcgcatcc accccgacgg ccgagttgac gggacccggg agaagagcga ccctttcatc       180
aagctacaac ttcaagcaga agagagagga gttgtgtcta tcaaaggagt gtgtgctaac       240
cgttacctgg ctatgaagga agatggaaga ttactggctt ctaaatgtgt tacggatgag       300
tgtttctttt ttgaacgatt ggaatctaat aactacaata cttaccggtc aaggaaatac       360
accagttggt atgtggcact gaaacgaact gggcagtata aacttggatc caaaacagga       420
cctgggcaga aagctatact ttttcttcca atgtctgcta agagctag                    468

<210> SEQ ID NO 30
<211> LENGTH: 155
<212> TYPE: PRT
<213> ORGANISM: Artificial Sequence
<220> FEATURE:
<223> OTHER INFORMATION: Amino acid sequence of FGF-2 CS1

<400> SEQUENCE: 30

-continued

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Leu Leu
            20                  25                  30

Tyr Cys Lys Asn Gly Gly Phe Phe Leu Arg Ile His Pro Asp Gly Arg
        35                  40                  45

Val Asp Gly Thr Arg Glu Lys Ser Asp Pro Phe Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 31
<211> LENGTH: 468
<212> TYPE: DNA
<213> ORGANISM: Artificial Sequence
<220> FEATURE:
<223> OTHER INFORMATION: Nucleic acid sequence encoding the amino acid sequence shown for SEQ ID NO:32

<400> SEQUENCE: 31

```
atggcagccg ggagcatcac cacgctgccc gccttgcccg aggatggcgg cagcggcgcc      60
ttcccgcccg ccacttcaa ggaccccaag ctgctgtact gcaaaaacgg gggcttcttc     120
ctgcgcatcc accccgacgg ccgagttgac gggacccggg agaagagcga cccttcatc     180
aagctacaac ttcaagcaga agagagagga gttgtgtcta tcaaaggagt gtgtgctaac     240
cgttacctgg ctatgaagga agatggaaga ttatatgctt ctaaatatgt tacggatgag     300
tgttcttttt tgaacgatt ggaagaaaat aactacaata cttaccggtc aaggaaatac     360
accagttggt atgtggcact gaaacgaact gggcagtata aacttggatc caaaacagga     420
cctgggcaga agctatact ttttcttcca atgtctgcta agagctag                   468
```

<210> SEQ ID NO 32
<211> LENGTH: 155
<212> TYPE: PRT
<213> ORGANISM: Artificial Sequence
<220> FEATURE:
<223> OTHER INFORMATION: Amino acid sequence of FGF-2 CS2

<400> SEQUENCE: 32

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Leu Leu
            20                  25                  30

Tyr Cys Lys Asn Gly Gly Phe Phe Leu Arg Ile His Pro Asp Gly Arg
        35                  40                  45

Val Asp Gly Thr Arg Glu Lys Ser Asp Pro Phe Ile Lys Leu Gln Leu
    50                  55                  60
```

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Tyr Ala Ser Lys Tyr
                85                  90                  95

Val Thr Asp Glu Cys Phe Phe Phe Glu Arg Leu Glu Glu Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155

<210> SEQ ID NO 33
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:34

<400> SEQUENCE: 33
atggcagccg ggagcatcac cacgctgccc gccttgcccg aggatggcgg cagcggcgcc      60
ttcccgcccg gccacttcaa ggaccccatc ctgctgtact gcaaaacgg gggcttcttc      120 ctgcgcatcc accccgacgg ccgagttgac gggacccggg acaagagcga ccctttcatc     180
aagctacaac ttcaagcaga agagagagga gttgtgtcta tcaaaggagt gtgtgctaac     240
cgttacctgg ctatgaagga agatggaaga ttatatgctt ctaaatatgt tacggatgag     300
tgtttctttt ttgaacgatt gcacgaaaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctag                  468

<210> SEQ ID NO 34
<211> LENGTH: 155
<212> TYPE: PRT
<213> ORGANISM: Artificial Sequence
<220> FEATURE:
<223> OTHER INFORMATION: Amino acid sequence of FGF-2 CS3

<400> SEQUENCE: 34

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Ile Leu Leu
            20                  25                  30

Tyr Cys Lys Asn Gly Gly Phe Phe Leu Arg Ile His Pro Asp Gly Arg
        35                  40                  45

Val Asp Gly Thr Arg Asp Lys Ser Asp Pro Phe Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Tyr Ala Ser Lys Tyr
                85                  90                  95

Val Thr Asp Glu Cys Phe Phe Phe Glu Arg Leu His Glu Asn Asn Tyr
            100                 105                 110

Asn Thr Tyr Arg Ser Arg Lys Tyr Thr Ser Trp Tyr Val Ala Leu Lys
        115                 120                 125

```
Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 35
<211> LENGTH: 468
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:36

<400> SEQUENCE: 35
atggcagccg ggagcatcac cacgctgccc gccttgcccg aggatggcgg cagcggcgcc      60
ttcccgcccg gccacttcaa ggaccccaag ctgctgtact gcaaaaacgg gggcttcttc     120
ctgcgcatcc accccgacgg ccgagttgac gggacccggg acaagagcga ccctttcatc     180
aagctacaac ttcaagcaga agagagagga gttgtgtcta tcaaaggagt gtgtgctaac     240
cgttacctgg ctatgaagga agatggaaga ttatatgcta tcaaaaacgt tacggatgag     300
tgtttctttt ttgaacgatt ggaagaaaat aactacaata cttaccggtc aaggaaatac     360
cccagttggt atgtggcact gaaacgaact gggcagtata aacttggatc caaaacagga     420
cctgggcaga agctatact tttttcttcca atgtctgcta gagctag                   468

<210> SEQ ID NO 36
<211> LENGTH: 155
<212> TYPE: PRT
<213> ORGANISM: Artificial Sequence
<220> FEATURE:
<223> OTHER INFORMATION: Amino acid sequence of FGF-2 CS4

<400> SEQUENCE: 36

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Leu Leu
            20                  25                  30

Tyr Cys Lys Asn Gly Gly Phe Phe Leu Arg Ile His Pro Asp Gly Arg
        35                  40                  45

Val Asp Gly Thr Arg Asp Lys Ser Asp Pro Phe Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Tyr Ala Ile Lys Asn
                85                  90                  95

Val Thr Asp Glu Cys Phe Phe Phe Glu Arg Leu Glu Glu Asn Asn Tyr
            100                 105                 110

Asn Thr Tyr Arg Ser Arg Lys Tyr Pro Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 37
<211> LENGTH: 468
<212> TYPE: DNA
<213> ORGANISM: Artificial Sequence
```

```
<220> FEATURE:
<223> OTHER INFORMATION: Nucleic acid sequence encoding the amino acid
      sequence shown for SEQ ID NO: 38

<400> SEQUENCE: 37
atggcagccg ggagcatcac cacgctgccc gccttgcccg aggatggcgg cagcggcgcc    60
ttcccgcccg gccacttcaa ggaccccatc ctgctgtact gcaaaaacgg gggcttcttc   120
ctgcgcatcc accccgacgg ccgagttgac gggacccggg acaagagcga ccctttcatc   180
aagctacaac ttcaagcaga agagagagga gttgtgtcta tcaaggagt gtgtgctaac    240 cgttacctgg ctatgaagga agatggaaga ttatatgcta tcaaaaacgt tacggatgag   300
tgtttctttt ttgaacgatt gcacgaaaat aactacaata cttaccggtc aaggaaatac   360
cccagttggt atgtggcact gaaacgaact gggcagtata aacttggatc caaaacagga   420
cctgggcaga aagctatact ttttcttcca atgtctgcta agagctag                468

<210> SEQ ID NO 38
<211> LENGTH: 155
<212> TYPE: PRT
<213> ORGANISM: Artificial Sequence
<220> FEATURE:
<223> OTHER INFORMATION: Amino acid sequence of FGF-2 CS5

<400> SEQUENCE: 38

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Ile Leu Leu
            20                  25                  30

Tyr Cys Lys Asn Gly Gly Phe Phe Leu Arg Ile His Pro Asp Gly Arg
        35                  40                  45

Val Asp Gly Thr Arg Asp Lys Ser Asp Pro Phe Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Tyr Ala Ile Lys Asn
                85                  90                  95

Val Thr Asp Glu Cys Phe Phe Phe Glu Arg Leu His Glu Asn Asn Tyr
            100                 105                 110

Asn Thr Tyr Arg Ser Arg Lys Tyr Pro Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

THERMOSTABLE FGF2 POLYPEPTIDE, USE THEREOF

FIELD OF THE INVENTION

The present invention relates to engineered Fibroblast Growth Factor 2 (FGF2, bFGF) having improved thermal stability compared to the wild-type and the use thereof in the cell biology research, regenerative medicine and related medical applications or cosmetics. The present invention further relates to a culture medium comprising FGF2 suitable for culturing a human pluripotent stem cells involving both human embryonic stem cells and induced pluripotent stem cells.

BACKGROUND OF THE INVENTION

Fibroblast Growth Factor 2 (FGF2, also known as basic FGF, bFGF) is a pleiotropic regulator of proliferation, differentiation, migration, and survival in a variety of cell types and is an essential component of media for human pluripotent stem cells (PSC) cultivation because it helps maintain the cells in the pluripotent state. Pluripotency is the ability of cells to undergo indefinite self-renewal and differentiate into all cell types of the human body. This property makes cells valuable for studying embryogenesis, for drug discovery, and for cell-based therapies. Other important biological activities of FGF2 that cover medicinal use include promotion of angiogenesis, promotion of wound healing, promotion of chondrogenesis or osteogenesis, and promotion of neurogenesis.

However, low stability and short half-life of the wild-type FGF2 is not practical for several applications, including cultivation of PSC. The half-life of wild-type molecule is less than 24 hours under conditions typically used to culture human PSC, necessitating frequent replacements, which is of concern in the industry from a cost perspective (Lotz, et al. 2013, PLoS One 8: e56289). A method for culturing a mammalian stem or progenitor cells in the presence of sustained concentration of FGF2 is provided in the patent document U.S. Pat. No. 8,481,308. Moreover, due to continuous FGF2 degradation, stem cells are exposed to fluctuation of its concentration, which may contribute to rapid decrease of proper signaling that is essential for pluripotency. The thermodynamic stability of a protein is of particular importance in therapeutic applications because unfolded or aggregated forms of a protein may be potentially toxic and immunogenic.

Traditionally FGF2 is stabilized by addition of heparin which protects FGF2 from denaturation by heat and acid, and also prolongs its half-life. However, heparin is produced by mast cells in the body so its use is not physiological in most cells/tissues regulated by FGF2 in vivo. Moreover, due to anticoagulation properties of heparin and risks of inducing allergic reactions, it is not suitable to use such preparations for medical and cosmetic purposes. Therefore, a need continues in the art for new and improved methods that will allow to obtain affordable FGF2 composition having higher stability and longer functional half-life without the need for heparin.

Patent document WO2013/082196 describes conjugates of heparin mimicking sulfonate polymers (such as poly (styrene sulfonate)) or copolymers (such as poly(styrene sulfonate-co-poly(polyethylene glycol methacrylate) and FGF2, in order to stabilize FGF2 while retaining its full growth factor activity. The stabilization of FGFs by addition of some agents describe several patent documents such as U.S. Pat. No. 7,754,686 (addition of a reducing agent to inhibit FGF oxidations), U.S. Pat. No. 5,202,311 (addition of sucrose octasulfate), U.S. Pat. No. 5,189,148 (addition of water-insoluble hydroxypropyl cellulose), EP0345660 (addition of glucan sulfate). However, the disadvantage of such preparations is, as in the case of FGF2 formulated with heparin, the presence of potentially harmful compounds which are not suitable for medical and day-care purposes.

Protein engineering offers powerful solution to stabilize proteins without additives. Accordingly, mutants of FGF1 and FGF2 that belong to the same subfamily are described that have enhanced stability and/or function. The biotechnological applications of FGF1 are even more limited compared to FGF2, mainly due to its high intrinsic instability.

US patent application No. 2008/038287 relates to the design, manufacture and use of FGF2 or FGF4 polypeptides having improved receptor specificity achieved by truncation of N-terminus and optionally N-terminal amino acid substitution. However, they neither teach nor support that mutation or truncation in N-terminal residues would affect thermostability of FGFs.

US patent application No. 2012/0225479 relates to engineered human FGF2 mutants with increased thermostability and the method of using the same in the culturing of embryonic stem cells. The authors employed substitutions Q65I, N111G and C96S of wild FGF2 sequence, identified by simple amino acid sequence alignment between FGF2 and stabilized FGF1 mutant reported by Zakrzewska et al. (Zakrzewska M, 2005 J Mol Biol). Described mutants show a certain level of stabilization but without maintaining its biological activity for longer term at higher temperature.

US patent application No. 2013/0236959 describes specific thermostable FGF2 K128N mutant. K128 is an amino acid that, in the case of wild-type FGF2, significantly contributes to heparin and heparan sulfate proteoglycan (HSPG) binding. Thus, amino acid substitution at this position decreases the ability of FGF2 to bind HSPG, which may negatively affect the specific biological activity of FGF2, since the binding of FGF2 to HSPG is one of the critical functional components in FGF receptor activation. The overall mechanism of FGF signaling involves heparin or HSPGs which act as co-receptors to facilitate FGF oligomerization and binding of FGF to its tyrosine kinase receptors (FGFR), leading to FGFR oligomerization and signaling. A substitution in heparin/HSPG binding domain is disclosed also in US patent application No. 2013/0157359. This application relates to the use of two variants of FGF1 having enhanced thermostability by introduction of three and four amino acid substitutions. Stabilization of FGF1 independent of heparin was achieved by mutating a residue K112 which is important to HSPG binding.

U.S. Pat. No. 8,461,111 relates to engineered FGF1 having improved functional half-life by introducing core packaging mutations.

U.S. Pat. No. 8,119,776 relates to engineered FGF1 having increased thermostability and mitogenic potency by substituting residues 12 and 134.

DISCLOSURE OF THE INVENTION

It is an object of the invention to provide FGF2 with thermostability that would significantly reduce cost of cultivations, may lead to improved quality of cultivated cells and less demanding operation. Moreover, it could be used in the regenerative medicine and related medical applications or cosmetics.

The drawbacks resulting from the state-of-the-art solutions are overcome by the present invention that presents a thermostable isolated polypeptide that possesses FGF2 activity and consists of FGF2 polypeptide having 85% sequence identity to a sequence SEQ ID NO: 2 or a fragment thereof. At the same time the FGF2 polypeptide comprises at least one amino acid substitution selected from R31L or H59F; or at least a combination of two substitutions R31L and H59F. It means that the polypeptide according to the invention always exhibits at least R31L or H59F substitution; or at least the combination of two substitutions R31L and H59F.

Advantageously subjected FGF-2 polypeptides or the fragments thereof according to the invention show stable and unchanged biological activity at high temperature for long time (for example see FIG. 11).

The thermostable FGF2 polypeptides or the fragments thereof according to the invention benefit especially from the fact that they are markedly more stable compared to wild-type FGF2. This stability is inherent to the FGF2; no additional compounds such as heparin have to be added. Even none of amino acid positions that are essential for biological activity of FGF2 are substituted or truncated. The subjected FGF2 mutants as well as fragments thereof can be used in clinical as well as in research practices.

The thermostable FGF2 polypeptides or the fragments thereof according to the invention possesses FGF2 activity and increased melting temperature by 1 to 20° C., preferably by 8 to 20° C., more preferably 14 to 20° C., compared to the wild-type FGF2 polypeptide. All 13 single point mutants were constructed, subcloned into expression vector pET28b, purified (purity ≥95% as judged by SDS-PAGE analysis) and subsequently characterized for melting temperature.

In an additional aspect, the present invention provides the FGF2 polypeptide having at least 85% sequence identity to SEQ ID NO:2 or fragments thereof, and comprising at least the amino acid substitution R31L.

Preferred embodiments of the invention disclose the thermostable FGF2 polypeptides, having SEQ ID NO: 2 or the fragment thereof comprising at least the amino acid substitution R31L.

The more preferred are the polypeptides comprising sequences selected from SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 or SEQ ID NO:28.

More preferred embodiments of the invention disclose the thermostable FGF2 polypeptide or the fragment thereof further comprising at least two or at least five or at least eight or at least ten amino acid substitutions selected from a group consisting of R31W, V52T, H59F, L92Y, C96Y, S109E, K30I, E54D, S94I, C96N, E108H, T121P in case that the essential substitution in the FGF2 polypeptide is R31L.

More preferred embodiments of the invention disclose the thermostable FGF2 polypeptide or the fragment thereof further comprising at least two or at least five or at least eight or at least ten amino acid substitutions selected from a group consisting of R31W, R31L, V52T, L92Y, C96Y, S109E, K30I, E54D, S94I, C96N, E108H, T121P in case that the essential substitution in the FGF2 polypeptide is H59F.

More preferred embodiments of the invention disclose the thermostable FGF2 polypeptide or the fragment thereof further comprising at least one or at least four or at least seven or at least nine amino acid substitutions selected from a group consisting of R31W, V52T, L92Y, C96Y, S109E, K30I, E54D, S94I, C96N, E108H, T121P in case that the essential substitutions in the FGF2 polypeptide is the combination of substitutions R31L and H59F.

More preferred embodiments of the invention disclose the polypeptide comprising: (a) three amino acid substitutions R31L, V52T, H59F, the most preferred is the polypeptide having SEQ ID NO:30, or (b) six amino acid substitutions R31L, V52T, H59F, L92Y, C96Y, S109E, the most preferred is the polypeptide having SEQ ID NO:32 or (c) nine amino acid substitutions K30I, R31L, V52T, E54D, H59F, L92Y, C96Y, E108H, S109E, the most preferred is the polypeptide having SEQ ID NO:34 or (d) nine amino acid substitutions R31L, V52T, E54D, H59F, L92Y, S94I, C96N, S109E, T121P, the most preferred is the polypeptide having SEQ ID NO:36 and (e) eleven amino acid substitutions K30I, R31L, V52T, E54D, H59F, L92Y, S94I, C96N, E108H, S109E, T121P, the most preferred is the polypeptide having SEQ ID NO:38.

Also muteins as described below should be considered as a part of the scope of the present invention.

The biological activity of FGF2 polypeptides, or fragments thereof, or muteins thereof according to the invention can be quantitatively expressed by $EC_{50}$ for the proliferation of NIH/3T3 cells in the range 0.1 to 5 ng/mL, preferably 0.5 to 3 ng/mL. The biological activity of FGF2 can be evaluated by a cultured fibroblast proliferation assay as previously described (Dubey, et al. 2007 J Mol Biol).

In a second aspect, the present invention provides the thermostable FGF2 polypeptide or the fragment thereof according to the invention that can be used in regenerative medicine (such as for example curing of wounds and ulcers, fracture healing and periodontal tissue regeneration), and in other medical applications (such as for example cancer treatment, therapy for cardiovascular diseases and treatment of mood disorders) or in cosmetics (such as for example hair stimulation, support of collagen synthesis and anti-aging treatment).

In a third aspect, the present invention provides a culture medium suitable for culturing a human pluripotent stem cells in a undifferentiated state, comprising an effective amount of the thermostable FGF2 polypeptide or the fragment thereof according the invention, in the range of 1.0 ng/μl to 100 ng/μl of culture medium. Preferably the subjected culture medium comprises subjected FGF2 polypeptide or the fragment thereof according to the invention comprising amino acid substitutions (a) R31L, V52T, H59F, the most preferred is the polypeptide having SEQ ID NO:30, or (b) R31L, V52T, H59F, L92Y, C96Y, S109E, the most preferred is the polypeptide having SEQ ID NO:32 or (c) K30I, R31L, V52T, E54D, H59F, L92Y, C96Y, E108H, S109E, the most preferred is the polypeptide having SEQ ID NO:34 or (d) R31L, V52T, E54D, H59F, L92Y, S94I, C96N, S109E, T121P, the most preferred is the polypeptide having SEQ ID NO:36 and (e) K30I, R31L, V52T, E54D, H59F, L92Y, S94I, C96N, E108H, S109E, T121P, the most preferred is the polypeptide having SEQ ID NO:38.

These and other features, objects and advantages of the present invention will become better understood from the description that follows. In the description, reference is made to the accompanying drawings, which form a part hereof and in which there is shown by way of illustration, not limitation, embodiments of the invention.

DETAILED DESCRIPTION OF THE INVENTION

Definitions

The definition of certain terms as used in this specification are provided below. Unless otherwise defined, all technical and scientific terms used herein have the same meaning as commonly understood by one of ordinary skill in the art to which this invention pertain.

As used herein, the term 'thermo stability' is synonymous with the term 'thermal stability' of the protein and encompasses thermodynamic and kinetic stabilities. Thermodynamic stability is related to the equilibrium between folded (native) and unfolded state of the protein and defined as the difference in Gibbs free energy between these two protein states.

As used herein, the term 'melting temperature' ($T_m$) of FGF2 protein refers to the temperature at which 50% of the protein is folded and 50% of the protein is unfolded. The melting temperature is a direct measure of the thermodynamic stability.

As used herein, the term 'half-life' of FGF2 protein refers to the amount of time it takes for the biological function of FGF2 protein to become reduced by half under defined process conditions. For example, the functional half-life may be based on the biological activity of FGF2 protein over time in inducing growth, proliferation and/or survival of cells. The half-life is a direct measure of the kinetic stability which is related to an energy barrier separating the native state from the non-functional protein forms (unfolded states, irreversibly-denatured protein).

As used herein, the term 'wild-type' refers to native FGF2 having most common amino acid sequence among members of a species. Herein, wild-type FGF2 is human FGF2 which is a 18 kDa protein with a length of 155 amino acids (SEQ ID NO:2).

As used herein, the term ' FGF2 polypeptide' refers to a polypeptide possessing FGF2 activity having at least 85% sequence identity to SEQ ID NO:2 or preferably having SEQ ID NO:2, and comprising at least one amino acid substitution selected from the group consisting of R31L or H59F; or at least the combination of two substitutions R31L and H59F, with $T_m$ increased by at least 1° C., preferably by at least 8° C., more preferably by at least 14° C. compared to the wild-type FGF2 protein. $T_m$ can be measured by any method suitable for determination of melting temperature as circular dichroism spectroscopy, differential scanning calorimetry and fluorescent thermal shift assay.

As used herein, the term '3-point FGF2 mutant' or "FGF2 CS1" refers to a FGF2 polypeptide having SEQ ID NO:2 or the fragment thereof comprising the following amino acid substitutions: R31L, V52T, H59F. Preferably it is the polypeptide having SEQ ID NO:30.

As used herein, the term '6-point FGF2 mutant' or "FGF2 CS2" refers to a FGF2 polypeptide having SEQ ID NO:2 or the fragment thereof comprising the following amino acid substitutions: R31L, V52T, H59F, L92Y, C96Y, S109E. Preferably it is the polypeptide having SEQ ID NO:32.

As used herein, the term '9-point FGF2 mutant' or "FGF2 CS3" refers to a FGF2 polypeptide having SEQ ID NO:2 or the fragment thereof comprising the following amino acid substitutions: K30I, R31L, V52T, E54D, H59F, L92Y, C96Y, E108H, S109E. Preferably it is the polypeptide having SEQ ID NO:34.

As used herein, the term '9-point FGF2 mutant' or "FGF2 CS4" refers to a FGF2 polypeptide having SEQ ID NO:2 or the fragment thereof comprising the following amino acid substitutions: R31L, V52T, E54D, H59F, L92Y, S94I, C96N, S109E, T121P. Preferably it is the polypeptide having SEQ ID NO:36.

As used herein, the term '11-point FGF2 mutant' or "FGF2 CS5" refers to a FGF2 polypeptide having SEQ ID NO:2 or the fragment thereof or comprising the following amino acid substitutions: K30I, R31L, V52T, E54D, H59F, L92Y, S94I, C96N, E108H, S109E, T121P. Preferably it is the polypeptide having SEQ ID NO:38.

As used herein, the term 'FGF2 polypeptide' is synonymous with 'FGF2 mutant' and refers to a modified polypeptide sequence that has at least one different amino acid sequence exhibiting any of the substitutions according to the invention as compared to the wild-type sequence FGF2 SEQ ID NO:2.

As used herein, the term 'polypeptide' is synonymous with 'protein'.

As used herein, the term "FGF2 activity" is synonymous with the term "biological activity of FGF2". It intends the biological activity of FGF2 polypeptides, or fragments thereof, or muteins thereof according to the invention. They retain the cell binding portions and the heparin binding segments of the subjected FGF2 protein according to the invention. They are able to bind to at least one FGF receptor (FGFR) present on the surface of a cell, which is necessary for transducing the signal to the cell interior and to trigger growth, proliferation or survival of cultured cells relative to untreated control cells. Such cells may include, for example, cells of mesenchymal origin in general, fibroblasts, neuroblasts, glial cells and other cells of the neural origin, smooth muscle cells, endothelial cells etc., known in the art to express one or more FGFRs or to respond to FGF proteins. The FGFR includes various isotypes of the receptor including soluble versions comprising the extracellular domain and lacking the transmembrane and kinase domains. Biological activity can be measured by methods known in the art, for example as cell proliferation and/or substrate phosphorylation.

As used herein, the term 'fragment' refers to functional fragments of the FGF2 polypeptide according to the invention possessing FGF2 activity. Furthermore it refers to functional fragments of the FGF2 polypeptide having at least 85% sequence identity to the sequence SEQ ID NO:2. The fragment of FGF2 polypeptide exhibits also at least one or more substitutions according to the invention. The preferred is at least 96%, 97%, 98%, 99% or 100% sequence identity. The fragment is intended a polypeptide consisting of only a part of the intact polypeptide sequence and structure, and there can be a C-terminal deletion or N-terminal deletion of the variant. Such functional fragments retain the cell binding portions and the heparin binding segments of the subjected FGF2 protein according to the invention. The fragments of subjected FGF2 protein according to the invention retain the desired properties, thus their $T_m$ is increased by at least 1° C., preferably by at least 8° C., more preferably by at least 14° C. compared to the wild type FGF2 as well as they are able to bind to at least one FGF receptor present on the surface of a cell and to trigger growth, proliferation or survival of cultured cells relative to untreated control cells.

As used herein, the term 'mutein' refers to functional muteins of FGF2 protein or fragments thereof according to the invention. Furthermore it refers to functional muteins of a polypeptide having at least 85% sequence identity to the sequence SEQ ID NO:2 with exhibition any of the substitutions according to the invention. The preferred is at least 96%, 97%, 98%, 99% or 100% sequence identity. It means their mutated forms that retain any of possible substitutions of amino acids as described above for FGF2 protein according to the invention and at least 85% or more of the residues of the sequence SEQ ID NO: 2. Such functional mutein retains the biological activity of the FGF2 of this reference sequence. Preferably, the mutations are substitutions using L-amino acids, wherein one amino acid is replaced by another biologically similar amino acid. Examples of conservative substitutions include the substitution of one hydrophobic residue for another, or the substitution of one charged or polar residue for another. Preferably, substitutions are introduced at the FGF2 N-terminus, which is not associated with biological activity.

As used herein, the term 'sequence identity' intends the same amino acid residues are found within FGF2 protein according to the invention as defined above. The FGF2 protein that serves as references when a specified, contiguous segment of the amino acid sequence of FGF2 protein is aligned and compared to the amino acid sequence of the particular corresponding reference molecule. The percentage of sequence identity is calculated by determining the number of positions at which the identical amino acid residue occurs in both sequences to yield the number of matched positions, dividing the number of matched positions by the total number of positions in the segment undergoing comparison to the reference molecule, and multiplying the result by 100 to yield the percentage of sequence identity. Methods of sequence alignment are well known in the art. The reference sequence used herein refers to a particular corresponding human FGF2 protein according to the invention. In mammalian species such as, e. g. mouse, rat, rabbit, primate, pig, dog, cow, horse, and human, FGF2 is highly conserved and shows at least 85% sequence identity across a wide range of species. The preferred is at least 96%, 97%, 98%, or 99% or 100% sequence identity. A person skilled in the art will understand that remaining 15% or less of amino acids along the length of the FGF2 protein according to the invention is variable due to, for example, using different source of FGF2 species or addition of suitable non-FGF peptide sequence or tag generally known in the art etc. A FGF2 protein according to embodiments of the present invention having at least 85% identity to the wild-type FGF2 is unlikely to include proteins other than those resembling FGF2 since other members of the FGF family generally have much lower sequence identity.

As used herein, the term 'effective amount' intends the amount necessary to maintain pluripotent stem cells with an undifferentiated morphology for at least 5 passages.

As used herein, the term 'human pluripotent stem cells', involving both human embryonic stem cells and induced pluripotent stem cells, are characterized through their self-renewal capacity—ability to form identical progeny of themselves, and pluripotency which allows them to generate virtually all cell types of the human body.

As used herein, the term 'maintaining stem cells in pluripotent state' refers to maintaining cells in undifferentiated state with capacity to differentiate into virtually all cell types. The pluripotent state depends on the sternness-supporting cocktail of growth factors in which FGF2 is of major importance. FGF2 supports self-renewal by several ways: it directly activates the mitogen-activated protein kinase pathway, and indirectly promotes Transforming Growth Factor beta 1 and Activin signalling (Greber, et al. 2008, *Stem Cells* 25, 455-464). Through its roles in cell adhesion and survival, FGF2 complexly contributes to pluripotency of human PSCs (Eisellova, et al. 2009, *Stem Cells* 27, 1847-1857)

Description

The most appealing approach to overcome FGF protein instability is to alter protein properties by mutagenesis. By changing its amino acid sequence, a FGF protein may have higher thermal stability, increased half-life, as well as increased resistance to proteolytic degradation. Mutating proteins to optimize their properties is viable even for human therapeutic applications. Several mutant forms of proteins have been approved by the FDA for use as human pharmaceuticals.

The present disclosure provides FGF2 polypeptides according to the invention stabilized by protein engineering. The stabilizing mutations are predicted rationally by bioinformatic analysis and computational protein design. Hybrid method combining the information from evolutionary analysis and force-field calculations is enriched by smart-filtering and expert judgement. This approach leads to highly reliable in silico predictions of stabilizing substitutions. The mutants are consequently prepared by side-directed mutagenesis or screened from large saturation libraries by novel growth arrest assay. The final mutants are recombined by computational analysis and prepared by gene synthesis or mutagenesis.

In general, the gene coding for FGF2 is cloned and then expressed in transformed organisms, preferably a microorganism. The host organism expresses the foreign gene to produce FGF2 under expression conditions. Synthetic recombinant FGF2 can also be made in eukaryotes, such as yeast or human cells. Where the FGF2 may be the 146 amino acid form, the 153-155 amino acid form, or a mixture thereof depending upon the method of recombinant production (see U.S. Pat. No. 5,143,829).

The melting temperature is a direct measure of the thermodynamic stability. Examples of techniques used for measurement of melting temperature are circular dichroism (CD) spectroscopy, differential scanning calorimetry (DSC) and fluorescent thermal shift assay (TSA). CD spectroscopy is a label-free method suitable for monitoring the secondary structure and conformational changes of proteins. DSC is a thermal analysis technique that looks at how a protein's heat capacity is changed during thermal unfolding. TSA is high-throughput method that measures thermal stability of the protein tertiary structure using a fluorescent protein-binding probe which detects protein aggregation. Even though these techniques monitor different effects accompanying protein unfolding, the relative values calculated as the difference in $T_m$ between the reference wild type FGF2 and a FGF2 polypeptide according to the invention are comparable with the variation less than 0.5° C.

The disclosure presented herein, demonstrates, for the first time, that certain changes in wild type FGF2 result in a FGF2 mutants having higher thermal stability and longer half-life in human cell culture than the wild-type protein.

The FGF2 protein according to the invention used for insertion of substitutions described herein may be from any mammalian source such as, e. g. mice, rats, rabbits, primates, pigs, dogs, cows, horses, and humans provided they meet the criterion specified herein, that is, provided they become thermo-stabilized while retaining the desired biological activity of the wild-type FGF2. Preferably the subjected FGF2 protein is derived from a human source. However, any biologically active variants of mammalian FGF2 having at least 85%, and most preferably about 96%, 97%, 98%, 99% or more amino acid sequence identity to the amino acid sequence of the human FGF2 protein of SEQ ID NO:2 which serves as the basis for comparison, may be utilized in the present invention.

According to some embodiment, a stable FGF2 polypeptides according to the invention described herein may further include any additional non-FGF peptide sequence or tag generally known in the art, which may be used to facilitate its detection, purification, tagging to a particular tissue or cell, improved solubility, sustained activity, improved expression, etc.

The present disclosure also provides a characterization of the engineered subjected FGF2, a demonstration of the effects of the substitutions on the proteins, methods for using the proteins in the culture of human PSC, and a medium, containing at least one thermostable FGF2 protein described herein, suitable for culturing human PSC in an undifferentiated state. Human embryonic stem cells (ESC) employed in examples provided herewith were derived from blastocyst-stage embryos obtained with informed consent of donors. A well characterized human ESC line (Adewumi, et al. 2007, *Nat Biotechnol* 25, 803-816) CCTL14 (Centre of Cell Therapy Line) in passages 29-41 was used. As for human induced pluripotent stem cells (iPSC), AM13 line derived using reprogrammation of skin fibroblasts by Yamanaka's cocktail and Sendai virus transfection was used in passages 34-41 (Krutá, et al. 2014, *Stem Cells and Development* 23, 2443-2454).

The techniques and procedures described herein are generally performed according to the conventional methods, which are provided throughout this document. Generally, the nomenclature used herein and the laboratory procedures in molecular biology, biochemistry, analytical chemistry and cell culture are those well-known and commonly employed in the art.

Other features, objects and advantages of the invention will be apparent from the description and claims.

BRIEF DESCRIPTION OF DRAWINGS

The present invention will be better understood and aspects and advantages other than those set forth above will become apparent when consideration is given to the following detailed description thereof. Such detailed description makes reference to the following drawings, wherein:

FIG. 1. is the polypeptide of wild-type FGF2 (SEQ ID No.2).

FIG. 2 is the nucleotide sequence of wild-type Fgf2 [SEQ ID NO: 1] with upstream sequences in pET28b vector. Start codon is grey. His-tag is underlined by thick line, thrombin cleavage recognition site is in black and restriction sites NdeI and XhoI for cloning into pET28b expression vector are underlined by bold line. Wild-type Fgf2 coding sequence starts with ATG and stop codon is TAG.

EXAMPLES

Figure 3:
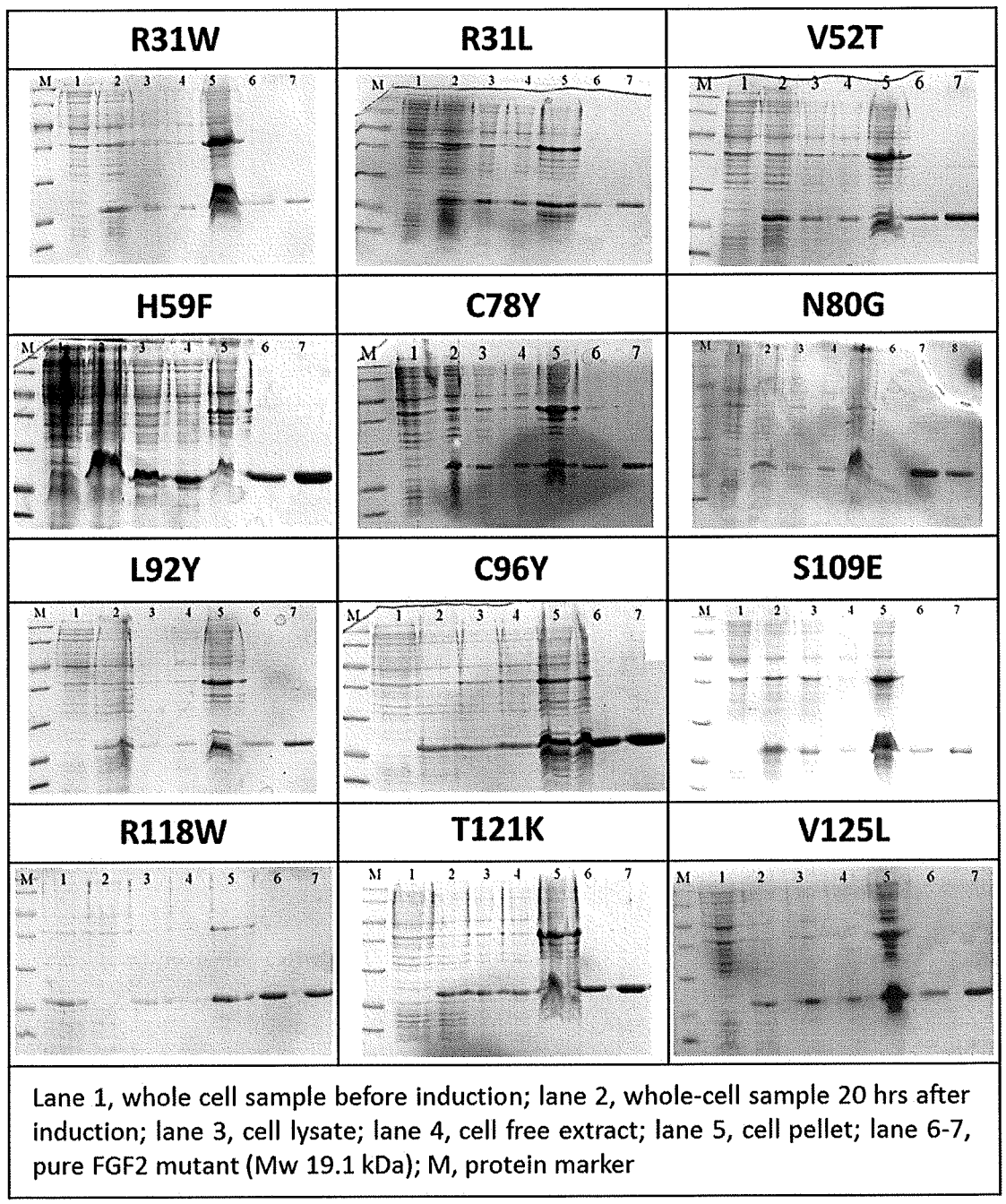
FIG. 3. shows the SDS-PAGE gels following expression and purification of single-point FGF2 mutants (R31W, R31L, V52T, H59F, C78Y, N80G, L92Y, C96Y, S109E, R118W, T121K, V125L). Protein marker: 116, 66.2, 45, 35, 25, 18.4, 14.4 kDa. Recombinant FGF2 mutants with 6×His tag and thrombin cleavage site have Mw of app. 19.1 kDa.

The following examples are presented in order to illustrate the embodiments of the present invention. Examples given are illustrative in nature only and not intended to be limiting. Although methods and materials similar or equivalent to those described herein can be used in the testing of the present invention, suitable methods and materials are described below.

Example 1. Prediction of Stabilizing Effect of Single-Point Mutations in FGF2 by Energy-Based Approach Available structures of FGF2 with resolution higher than 2.20 Å were downloaded from the RCSB Protein Data Bank (Berman et al., (2000). *Nucleic Acids Res.* 28, 235-242.). The structures were prepared for analyses by removing ligands and water molecules. One chain was chosen in the case of multiple chain structure. All the structures were renumbered so they start from the position 1. Protein side chains were minimized and scored to determine whether minimization passed correctly. Stability effects of all possible single-point mutations were estimated using the force-field calculations. ΔΔG free energies were collected and averaged over all used structures and subsequently averaged over all 20 mutations in a particular position. Evolutionary conservation was estimated using phylogenetic analysis of homologous sequences. Mutations with ΔΔG<−1.0 kcal/mol and conservation <8 were selected for further analysis. The best positions with only a limited influence on functional regions, e.g., heparin binding residues, were identified. Nine single-point substitutions were selected for experimental construction and characterization: R31W, R31L, H59F, C78Y, L92Y, C96Y, R118W, T121K and V125L (Table 1). The numbering of these mutants corresponds to the sequence of wild type human FGF2 (SEQ ID NO:2 below).

TABLE 1

The stabilizing mutations selected according to the free energy prediction, conservation analysis and visual inspection.

| Residue | Position | Mutation | ΔΔG [kcal/mol] | Conservation | Functional role |
|---------|----------|----------|----------------|--------------|-----------------|
| R | 31 | L | −3.6 | 7 | — |
| R | 31 | W | −4.0 | 7 | — |
| H | 59 | F | −2.6 | 3 | FGF-2 dimerization |
| C | 78 | Y | −1.5 | 3 | — |
| L | 92 | Y | −2.3 | 7 | — |
| C | 96 | Y | −3.0 | 3 | self-association |
| R | 118 | W | −1.6 | 3 | — |
| T | 121 | K | −1.5 | 7 | — |
| V | 125 | L | −1.7 | 7 | — |

ΔΔG: change in Gibbs free energy upon mutation

Example 2. Prediction of Stabilizing Effect of Single-Point Mutations in FGF2 by Evolution-Based Approach Multiple sequence alignment of FGF2 with related proteins was constructed. The FGF2 protein sequence was used as a query for PSI-BLAST (Altschul et al., (1997). *Nucleic Acids Res.* 25, 3389-3402) search against nr database of NCBI. Sequences collected after 3 iterations were clustered by CD-HIT (Li & Godzik, (2006). *Bioinformatics* 22, 1658-1659) at 90% identity threshold. Resulting dataset of more than 500 sequences was clustered with CLANS (Frickey & Lupas, (2004). *Bioinformatics.* 20, 3702-3704) using default parameters and varying P-value thresholds. Sequences clustered together with FGF2 at the P-value of 10$^{-30}$ were extracted and aligned with the MUSCLE program (Edgar, (2004). *BMC Bioinformatics.* 5, 113.). The final alignment comprising 238 sequences was used as an input for back-to-consensus analysis using the simple consensus approach. The analysis was performed using the consensus cut-off of 0.5, meaning that a given residue must be present at a given position in at least 50% of all analyzed sequences to be assigned as the consensus residue. Stability effects of all possible single-point mutations in FGF2 protein were estimated by free energy calculations. Only mutations with predicted average ΔΔG≤1 kcal/mol by both methods were considered as hot-spots for FGF2 stabilization. Functionally important sites of FGF2 were excluded as potentially deleterious mutations for biological function. Results of the back-to-consensus analysis are summarized in Table 2. The numbering corresponds to the sequence of wild-type human FGF2 (SEQ ID NO:2 below). Ten mutations were excluded based on the high value of predicted ΔΔG and three mutations were discarded from the design for their location at functionally important positions for the heparin binding. Finally, three single-point mutations passed all criteria and were selected for experimental construction and characterization: V52T, N80G and S109E.

SDS-PAGE in 15% polyacrylamide gel. Precipitation of proteins was minimized by dialysis against buffer containing 500-750 mM NaCl. Purification of FGF2 mutants by affinity chromatography resulted in homogeneous proteins with purity higher than 90% as judged by SDS PAGE analysis (FIG. 3). The yields of purified FGF2 mutants ranged from 15 to 90 mg·L$^{-1}$.

TABLE 2

Back-to-consensus mutations identified in FGF2 using 50% consensus cut-off. Mutations selected for experimental construction are V, N, and S.

| Residue | Position | Freq | Res_TOP | Freq_TOP | ΔΔG [kcal/mol] | Functional role |
|---|---|---|---|---|---|---|
| P | 22 | 0.10 | L | 0.59 | — | — |
| K | 27 | 0.11 | R | 0.52 | — | interface |
| R | 42 | 0.22 | Q | 0.53 | 3.04 | — |
| V | 52 | 0.13 | T | 0.53 | −0.70 | — |
| Q | 63 | 0.14 | E | 0.61 | 1.37 | interface, FGF2 dimerization |
| E | 67 | 0.11 | V | 0.71 | −0.39 | interface, FGF2 dimerization |
| A | 79 | 0.14 | S | 0.58 | 1.22 | — |
| N | 80 | 0.18 | G | 0.56 | −0.03 | — |
| K | 86 | 0.06 | N | 0.71 | 1.67 | self-association |
| A | 93 | 0.27 | G | 0.53 | 2.22 | — |
| S | 109 | 0.07 | E | 0.69 | 0.51 | — |
| K | 128 | 0.15 | N | 0.51 | 1.22 | heparin binding, self association |
| R | 129 | 0.14 | K | 0.58 | −0.20 | heparin binding, self association, interface |
| K | 138 | 0.36 | R | 0.53 | 0.62 | heparin binding |
| L | 147 | 0.2 | H | 0.68 | 1.10 | — |
| M | 151 | 0.13 | R | 0.55 | 1.92 | interface |

Freq: frequency of a given FGF-2 residue at a given position of the multiple sequence alignment; RES_Top: the most conserved residue at a given position of the multiple sequence alignment; Freq_TOP: frequency of the most conserved residue at a given position of the multiple sequence alignment; ΔΔG: change in Gibbs free energy upon mutation.

Example 3: Construction of Twelve Single Point Mutants of FGF2 and their Purification to Homogeneity by Affinity Chromatography Mutants FGF2 R31W, R31L, V52T, H59F, C78Y, N80G, L92Y, C96Y, S109E, R118W, T121K and V125L were commercially synthesized and subcloned in the NdeI and XhoI sites of pET28b-His-Thrombin downstream inducible T7 promotor. Resulting constructs were transformed into *Escherichia coli* Dh5α competent cells. Cells were plated on agar plates with kanamycin (50 μg·mL$^{-1}$) and grown overnight at 37° C. Plasmids were isolated and nucleotide sequences were confirmed by commercial sequencing. *E. coli* BL21(DE3) cells were transformed with expression vectors, plated on agar plates with kanamycin and grown overnight at 37° C. Single colonies were used to inoculate 10 mL of LB medium with kanamycin (50 μg·mL$^{-1}$) and cells were grown overnight at 37° C. Overnight culture was used to inoculate 200 mL of LB medium with kanamycin. Cells were cultivated at 37° C. The expression was induced with isopropyl β-D-1-thiogalactopyranoside (IPTG) to a final concentration of 0.25 mM. Cells were then cultivated overnight at 20° C. At the end of cultivation, biomass was harvested by centrifugation and washed by buffer (20 mM di-potassium hydrogenphosphate and potassium dihydrogenphosphate, pH 7.5, 0.5 M NaCl, 10 mM imidazole). Cells in suspension were disrupted by sonication and cell lysate was centrifuged. Proteins were purified from crude extracts using single step nickel affinity chromatography. The presence of proteins in peak fractions was proved by

Figure 4:
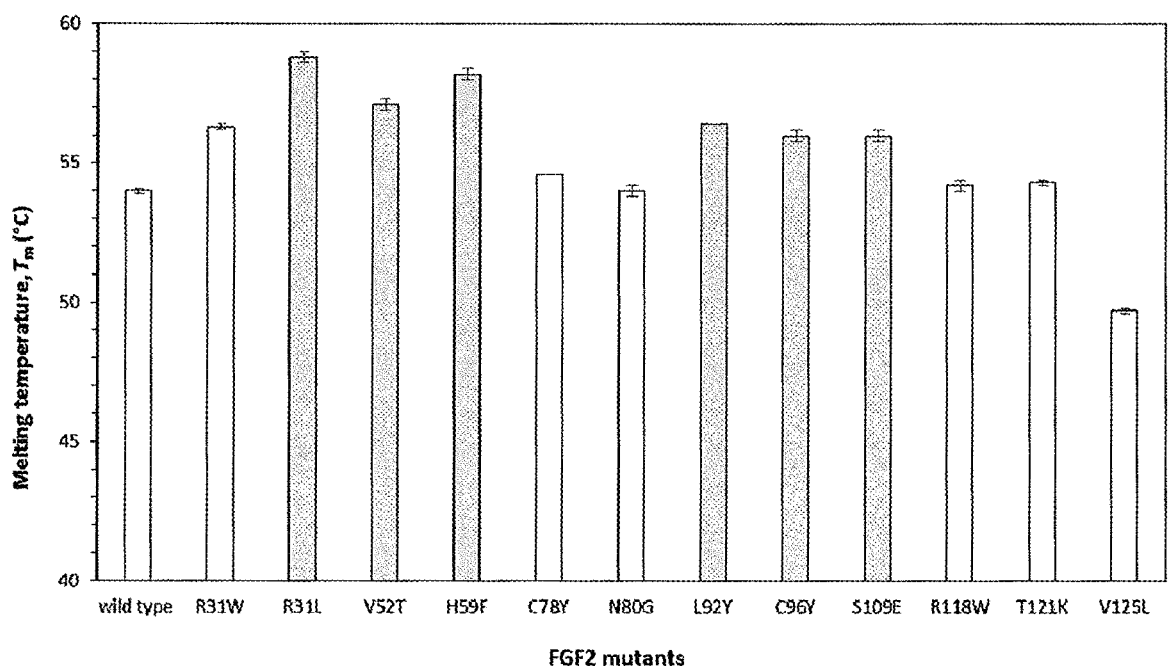
FIG. 4. shows the comparison of thermostability of individual single point FGF2 mutants (R31W, R31L, V52T, H59F, C78Y, N80G, L92Y, C96Y, S109E, R118W, T121K, V125L) measured by differential scanning calorimetry (DSC). Mutations selected for construction of combined mutants are highlighted in grey.

Example 4: Determination of Thermostability of Single-Point FGF2 Mutants by Differential Scanning Calorimetry The thermostability of single-point FGF2 predicted by energy- and evolution-based approaches was determined by differential scanning calorimetry (DSC) assay. Thermal unfolding of 1.0 mg/mL protein solutions in 50 mM phosphate buffer (pH 7.5) with 500-750 mM sodium chloride was followed by monitoring the heat capacity using the VP-capillary DSC system. The measurements were performed at the temperatures from 20 to 80° C. at 1° C./min heating rate. $T_m$ was determined as the temperature at which the heat capacity curve reached the maximum value. Results are shown in Table 4 and FIG. 4.

TABLE 4

Thermostability of FGF2 mutants determined by differential scanning calorimetry. Mutations selected for construction of combined 3- and 6-point mutants are R31L, V52T, H59F, L92Y, C96Y, and S109E.

| Mutant | $T_m$ (° C.)[1] | $\Delta T_m$ (° C.) | Prediction approach |
|---|---|---|---|
| wild type FGF2 | 54 | — | — |
| R31W | 56 | 2 | energy-based |
| R31L | 59 | 5 | energy-based |
| V52T | 57 | 3 | evolution-based |
| H59F | 58 | 4 | energy-based |
| C78Y | 55 | 1 | energy-based |
| N80G | 54 | 0 | evolution-based |
| L92Y | 56 | 2 | energy-based |
| C96Y | 56 | 2 | energy-based |

TABLE 4-continued

Thermostability of FGF2 mutants determined by differential scanning calorimetry. Mutations selected for construction of combined 3- and 6-point mutants are R31L, V52T, H59F, L92Y, C96Y, and S109E.

| Mutant | $T_m$ (° C.)[1] | $\Delta T_m$ (° C.) | Prediction approach |
|---|---|---|---|
| S109E | 56 | 2 | evolution-based |
| R118W | 54 | 0 | energy-based |
| T121K | 54 | 0 | energy-based |
| V125L | 50 | −4 | energy-based |

$T_m$: melting temperature; $\Delta T_m$: change in melting temperature upon mutation; [1]The average from three independent experiments is presented (standard deviations were less than 10%).

This example demonstrates that the in-silico prediction methods of the present disclosure are useful for prediction of stabilizing mutations in FGF2. Mutations improving $T_m$ by at least 2° C. were combined employing free energy calculations in 3-point (R31L, V52T and H59F) and 6-point (R31L, V52T, H59F, L92Y, C96Y and S109E) mutants FGF CS1 and FGF2 CS2, respectively (see Example 5).

Figure 5:
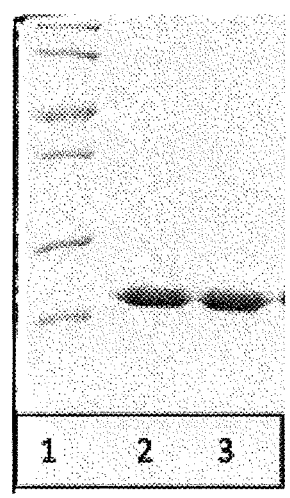
FIG. 5. is SDS-PAGE of purified FGF2 CS1 and CS2 mutants. Lane 1, protein marker (116, 66.2, 45, 35, 25, 18.4, 14.4 kDa); lane 2, purified FGF2 CS1 with 6×His tag and thrombin cleavage site of molecular weight 19.1 kDa, and lane 3, purified FGF2 CS2 with 6×His tag and thrombin cleavage site of molecular weight 19.1 kDa.
Figure 6:
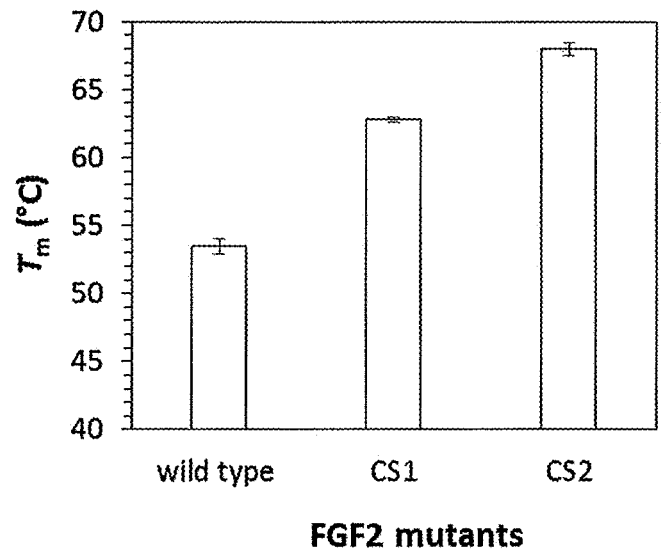
FIG. 6. shows the comparison of thermostability of wild-type FGF2 with FGF2 CS1 and FGF2 CS2 mutants. Melting temperature ($T_m$) was determined using DSC.

Example 5: Construction, Purification and Thermostability Analysis of 3-Point FGF2 CS1 and 6-Point FGF2 CS2 Mutants Multiple-point mutants of FGF2 were commercially synthesized and subcloned in the NdeI and XhoI sites of pET28b-His-Thrombin downstream inducible T7 promotor (mutated nucleotide and polypeptide sequences are shown in SEQ ID NO:29 to SEQ ID NO:32 below). Resulting constructs were transformed into *E. coli* Dh5α competent cells. Cells were plated on agar plates with kanamycin (50 µg·mL⁻¹) and grown overnight at 37° C. Plasmids were isolated and nucleotide sequences were confirmed by commercial sequencing. *E. coli* BL21(DE3) cells were transformed with expression vectors, plated on agar plates with kanamycin and grown overnight at 37° C. Single colonies were used to inoculate 10 mL of LB medium with kanamycin (50 µg·mL⁻¹) and cells were grown overnight at 37° C. Overnight culture was used to inoculate 200 mL of LB medium with kanamycin. Cells were cultivated at 37° C. The expression was induced with IPTG to a final concentration of 0.25 mM. Cells were then cultivated overnight at 20° C. At the end of cultivation, biomass was harvested by centrifugation and washed by buffer (20 mM di-potassium hydrogenphosphate and potassium dihydrogenphosphate, pH 7.5, 0.5 M NaCl, 10 mM imidazole). Cells in suspension were disrupted by sonication and cell lysate was centrifuged. Proteins were purified from crude extracts using single step nickel affinity chromatography. The presence of proteins in peak fractions was proved by SD S-PAGE in 15% polyacrylamide gel (FIG. 5). Precipitation of proteins was minimized by dialysis against buffer containing 750 mM NaCl. The yields of both mutants were about 20 mg/L of culture. DSC was used to characterize protein thermal stability. FGF2 mutants were diluted to 1.0 mg·mL⁻¹ for DSC experiments. DSC data collection was performed over a temperature range of 20° C.-100° C. $T_m$ were evaluated as the top of the Gaussian curve after manual setting of the baseline. FGF2 CS1 and CS2 mutants exhibited $T_m$ 62.8 and 68.0° C., respectively (FIG. 6).

Figure 7:
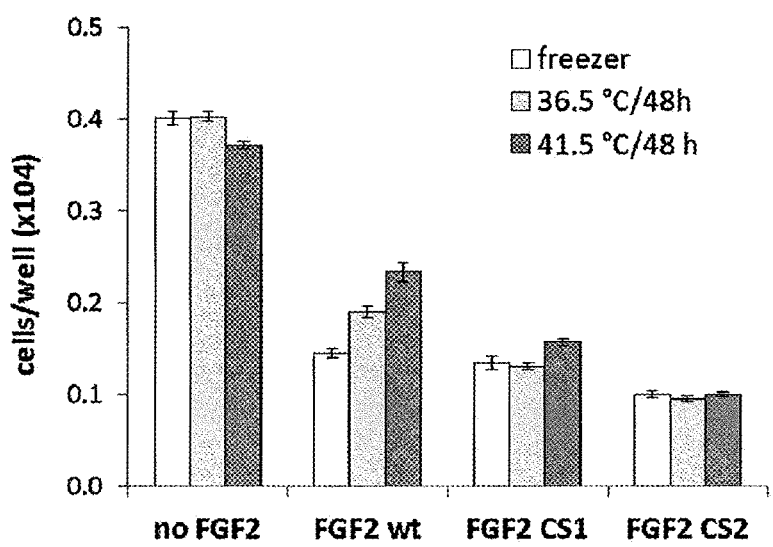
FIG. 7. shows the ability of wild-type FGF2, FGF2 CS1 and FGF2 CS2 to inhibit RCS cells proliferation after two-days incubation at 36.5 and 41.5° C. RCS cells were seeded in 96-well plates. The data represent average of six wells with the indicated standard deviation.

Example 6: Thermostability Determination of 3- and 6-Point FGF2 Mutants Using Rat Chondorsarchoma Growth-Arrest Assay Rat chondorsarcoma (RCS) cells is an immortalized phenotypically stable cell line that responds to minute concentrations of FGFs with potent growth arrest accompanied by marked morphological changes and extracellular matrix degradation. FGF receptor (FGFR) functions as an inhibitor of cell proliferation in this cell line. In order to inhibit cell proliferation, FGF mutants have to specifically induce FGFR signal transduction allowing the measuring of FGF activity reflected by the concentration dependence of induced growth arrest. The major advantage of the RCS assay is the exclusion of toxic chemicals and false-positive hits (Krejčí, et al., 2007 *Invest New Drugs*, 25: 391-395.). The high-throughput growth arrest experiment was performed in a 96-well plate format with the cellular content determined by simple crystal violet staining. Media with or without mutated FGF2 in approximate concentration 40 ng/mL were incubated at 36.5 and 41.5° C. for 48 hours and mixed every 12 hours within this period. To evaluate degradation of FGF2 mutants, preincubated media was mixed with mutated FGF2 as a fresh control. RCS cells were seeded in concentration 250 cells per well in 96-well plate, one day before the treatment. Cells were treated with both preincubated FGF2 and fresh control for each FGF2 mutants at a final concentration 20 ng/mL for 4 days. Cells were washed with PBS, fixed with 4% paraformaldehyde, washed again and stained with 0.025% crystal violet for 1 hour. Coloured cells were 3 times washed with distilled water. Colour from cells was dissolved in 33% acetic acid. Absorbance was measured at 570 nm. Results of RCS growth-arrest assay are shown in FIG. 7. This example demonstrates that the ability of 6-point FGF2 CS2 mutant to inhibit RCS cells proliferation is unaffected even after two-day incubation at 41.5° C. By contrast, the biological activity of the wild-type FGF2 is reduced already after incubation at 36.5° C.

Figure 8:
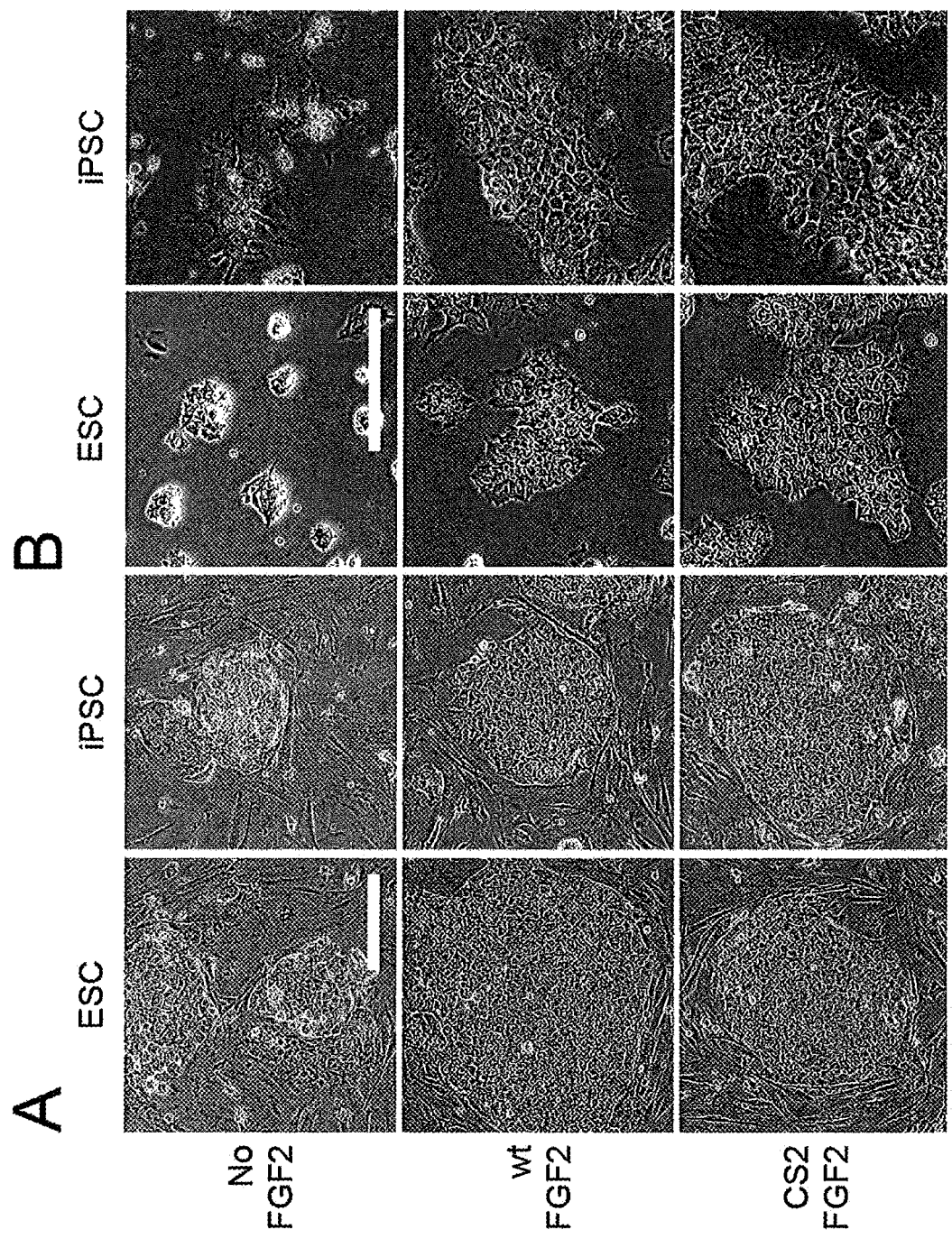
FIG. 8. demonstrates that FGF2 CS2 maintains undifferentiated morphology of human PSC. Human PSC, both ESC (CCTL14) and iPSC (AM13), were propagated either as colonies with feeder layer (A) or as monolayers on Matrigel (B). While withdrawal of exogenous FGF2 caused significant growth retardation, both of wild-type FGF2 and FGF2 CS2 were capable to give rise to colonies (A) and monolayers (B) with undifferentiated morphology. Scale bars, 100 μm.
Figure 9:
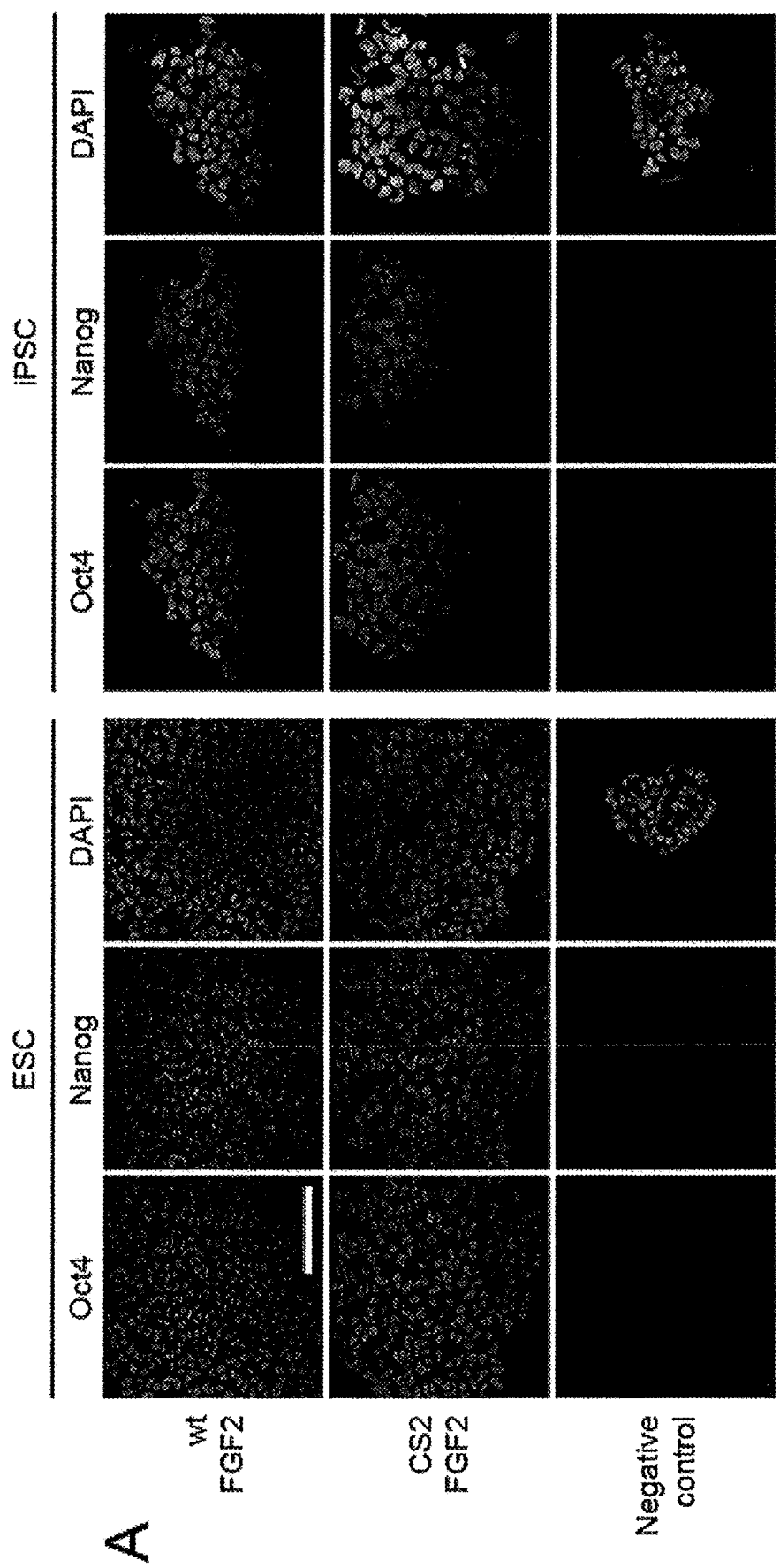
FIG. 9. demonstrates that FGF2 CS2 maintains pluripotency marker expression of human PSC. Human PSC, both ESC (CCTL14) and iPSC (AM13), were propagated either as colonies with feeder layer (A) or as monolayers on Matrigel (B). After five passages in each of the tested conditions, cells were immunostained for pluripotency markers Oct4 and Nanog. Negative controls were incubated without primary antibodies. Wild-type FGF2 and FGF2 CS2 supported expression of Oct4 and Nanog equally. Scale bars, 100 μm.
Figure 9:
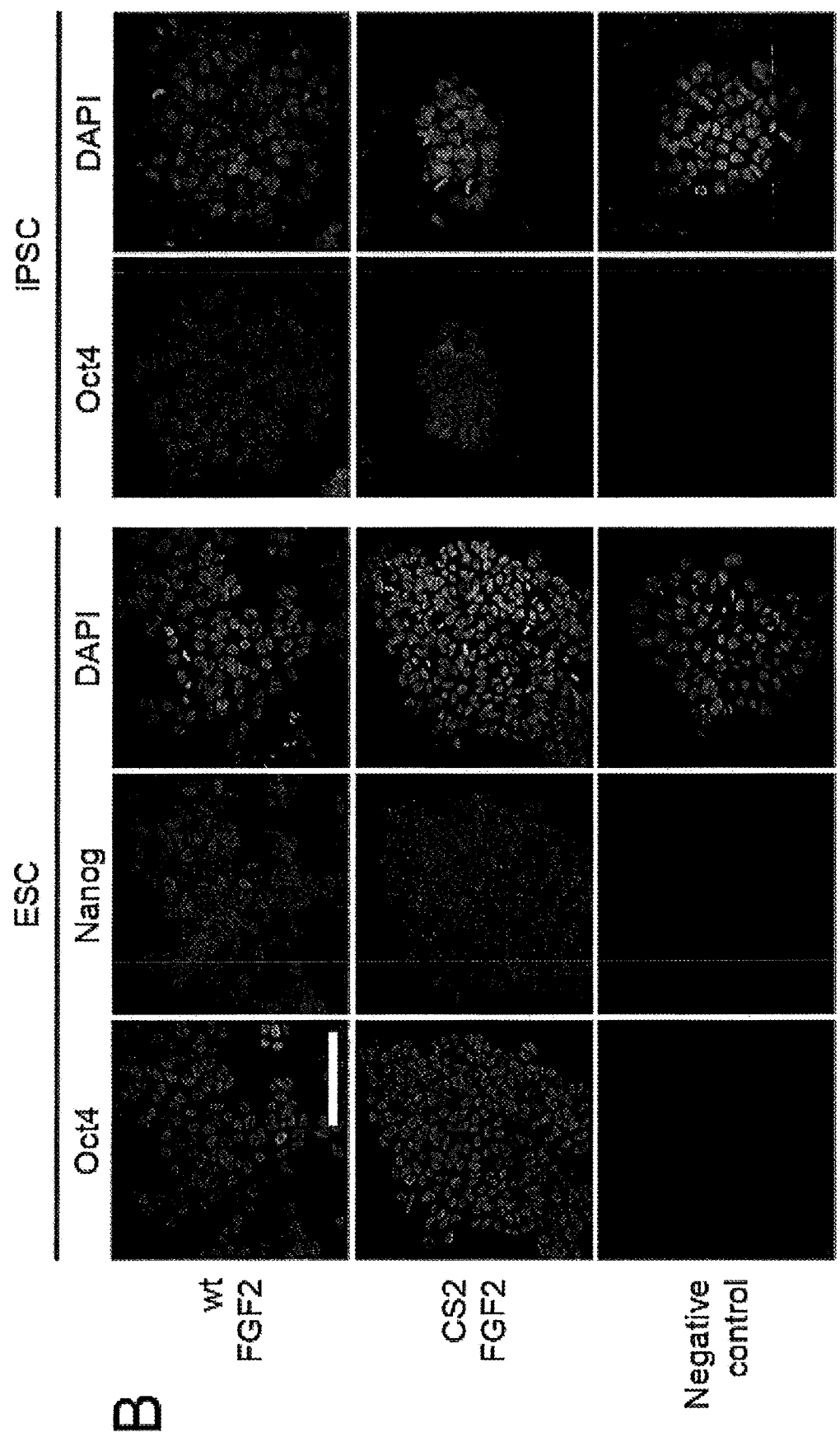
Figure 14:
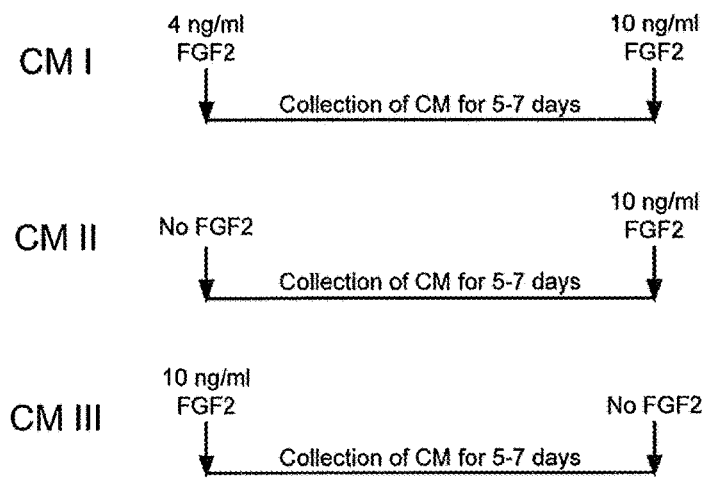
FIG. 14. shows the preparation of conditioned medium (CM). For preparation of standard CM, the complete human PSC medium was conditioned by mitotically inactivated mouse embryonic fibroblast (mEF) for 5-7 consecutive days and then supplemented by 10 ng/mL of FGF2 to restore growth factor concentration due to its degradation (CM I). For most of the experiments, the CM was prepared out of human PSC medium lacking FGF2, and only the final product was supplemented by 10 ng/mL of the desired FGF2 (CM II). Alternatively, to test the long-term thermostability of FGF2, the CM is prepared out of medium containing 10 ng/mL of FGF2 with no supplementation afterwards (CM III).

Example 7: Thermo-Stabilized 6-Point FGF2 CS2 Supports Undifferentiated Growth of Human Pluripotent Stem Cells To evaluate the ability of the thermo-stabilized FGF2 CS2 mutant to support long-term propagation of undifferentiated human pluripotent stem cells (PSC), two culture systems were used: (i) the colony growth in the presence of mouse embryonic fibroblast (mEF) feeder layer and (ii) the feeder-free monolayer growth on Matrigel™ hESC-qualified Matric (BD Biosciences). In feeder-dependent conditions, the medium consisted of DMEM/F12 (1:1) supplemented with 15% KnockOut Serum Replacement, 1% MEM Non-essential Amino Acids, 0.5% Penicillin-Streptomycin, 100 µM β-mercaptoethanol and 4 ng/mL of wild-type FGF2 or FGF2 CS2 mutant. In the feeder-free monolayer system, the mEF-conditioned medium is required for human PSC growth. For that, the culture medium was supplemented with the tested FGF2s (10 ng/mL) only after being conditioned by feeder cells (CM II, FIG. 14). Human PSC were grown in each of the tested conditions for five passages, and the morphology of cells as well as the expression of pluripotency markers Oct4 and Nanog was monitored. Human PSC maintained in the culture medium without FGF2 gave rise to small differentiated colonies indicating important role of FGF2 in the maintenance of the undifferentiated state of human PSC. When grown in the presence of both tested FGF2s, human PSC displayed typical morphology—tightly packed colonies when grown with feeder cells and high ratio of nucleus to cytoplasm in both culture systems (FIG. 8). No differences among wild-type FGF2 and 6-point FGF2 mutant regarding cell morphology was observed. To examine the pluripotency status of human PSC in more details, the expression of pluripotency markers Oct4 and Nanog was tested immunocytochemically. No differences in the amounts or patterns of expression of either Oct4 or Nanog were observed in any of the tested conditions (FIG. 9).

Figure 10:
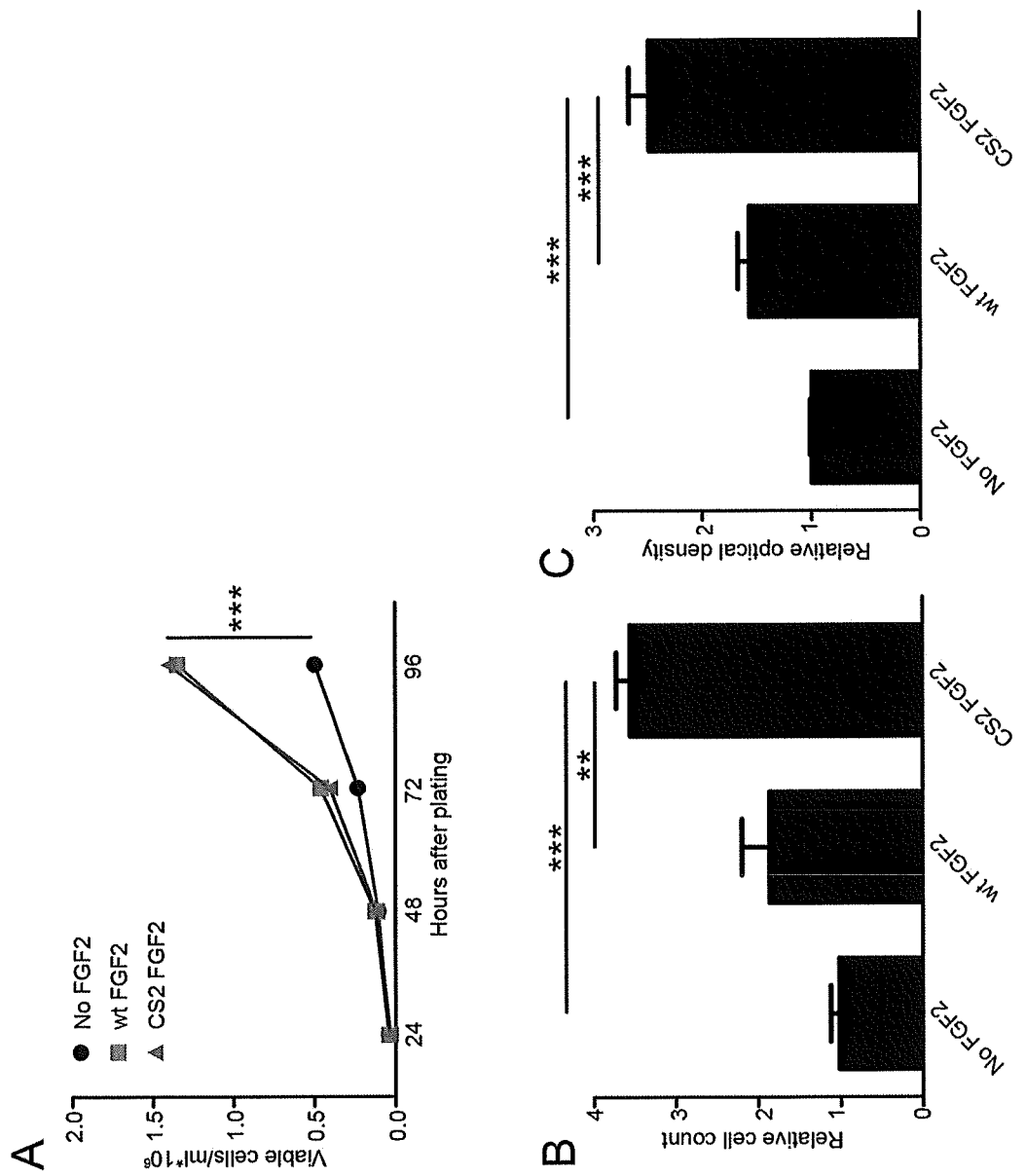
FIG. 10. demonstrates that FGF2 CS2 supports proliferation of human ESC. (A) Human ESC (CCTL14) were propagated in each of the tested FGF2, and the cell numbers were counted for four consecutive days. Representative result of two experiments is shown. Each data point shows mean±SEM of three wells. (B, C) Feeder-free monolayers of human ESC (CCTL14) were adapted to each of the tested FGF2 for five passages. Cells were then counted three days after plating and plotted as relative cell counts (B; n=2). Alternatively, cells were counterstained with crystal violet six days after plating and the results were plotted as relative optical densities (C; n=3). Columns show means, error bars show SEM. Student's t-test, *p<0.001, p<0.01, *p<0.05

Example 8: Thermo-Stabilized 6-Point FGF2 CS2 Stimulates Proliferation of Human Pluripotent Stem Cells To determine the proliferation rate, two approaches were used. First, the numbers of feeder-free human ESC were counted for four consecutive days after plating. Both tested FGF2 supported growth of human ESC with similar efficiency (FIG. 10A). To test the long-term supportive capacity of FGF2, feeder-free human ESC were adapted to each of the tested FGF2 for five passages. Then, either direct cell counts (FIG. 10B) or the optical density of the crystal violet counter stained cells (FIG. 10C) was used to measure proliferation. In these assays, 6-point FGF2 CS2 mutant supported proliferation of human ESC better than wild-type FGF2. The data demonstrate clear pro-proliferative effect of the thermo-stabilized FGF2 CS2, both during short-term and prolonged propagation.

Example 9: Thermo-Stabilized 6-Point FGF2 CS2 Maintains its Biological Activity During Prolonged Incubation at 37° C.

Figure 11:
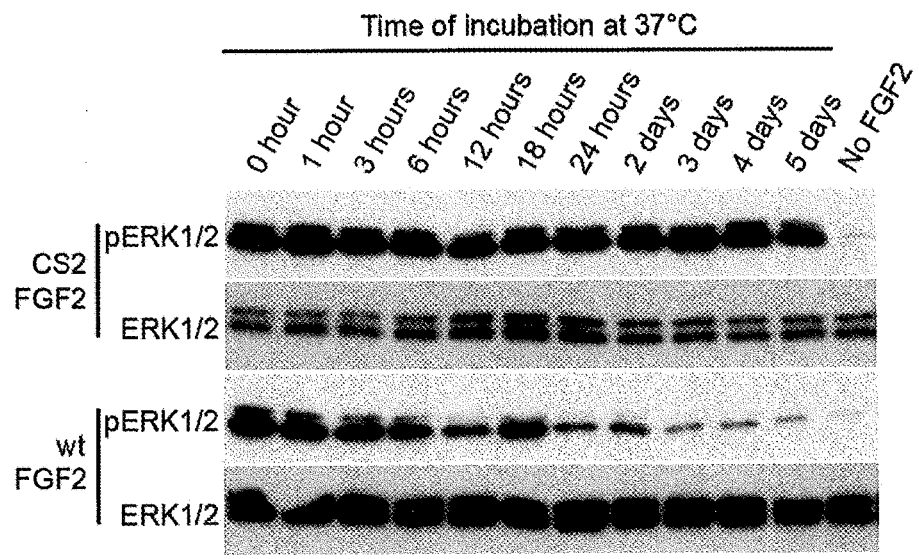
FIG. 11. shows the capacity of FGF2 CS2 to remain its biological activity during prolonged incubation at 37° C. Mouse embryonic fibroblast conditioned medium (CM) prepared without exogenous FGF2 was supplemented with 10 ng/mL FGF2 and incubated at 37° C. for 1 h, 3 h, 6 h, 12 h, 24 h, 2 d, 3 d, 4 d or 5 d. Then, FGF2-starved human ESC (CCTL14) were treated with CM containing heat-preincubated FGF2 for two hours and immunoblotted for phosphorylated ERK1/2. Total ERK1/2 levels were used as loading controls. While the biological activity of wild type FGF2 declined with time of heat-preincubation, the thermo-stabilized FGF2 CS2 retained full biological activity even after five days at 37° C. Representative results of four different experiments are shown.

FGF-receptors and their downstream effectors including ERK1/2 are activated upon treatment with FGF2, contributing to pluripotency of human PSC (Dvorak, et al. 2005, *Stem Cells* 25, 1200-1211.; Eiselleova, et al. 2009, *Stem Cell* 27, 1847-1857). As the biological activity of FGF2 decreases at 37° C., ERK1/2 phosphorylation declines and human PSC easily become primed to differentiation. To test the thermal stability of wild-type FGF2 and FGF2 CS2 mutant, CM prepared without FGF2 was supplemented with 10 ng/mL of desired FGF2 and incubated at 37° C. for 1 h, 3 h, 6 h, 12 h, 24 h, 2 d, 3 d, 4 d or 5 d. Then, FGF2-starved human ESC were treated with CM containing heat-preincubated FGF2 for two hours and western blotted for phosphorylated ERK1/2. While the biological activity of wild-type FGF2 declined with time of heat-preincubation, the thermo-stabilized FGF2 CS2 mutant retained full biological activity even after five days at 37° C. (FIG. 11).

Example 10: Daily Change of the Culture Medium is not Required with Thermo-Stabilized FGF2 CS2

Figure 12:
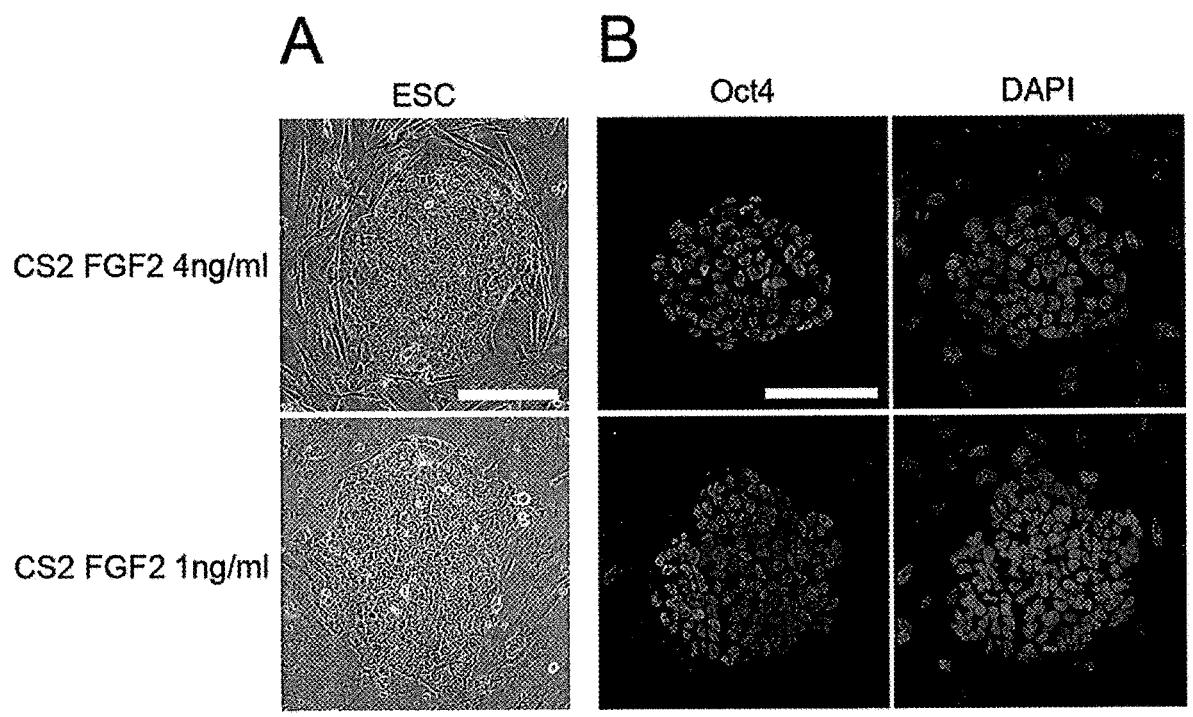
FIG. 12. demonstrates that FGF2 CS2 maintains pluripotent human ESC without need of daily medium change. Human ESC (CCTL14) colonies were grown in the presence of thermo-stabilized FGF2 CS2 for 5 passages, either in standard (4 ng/mL) or decreased (1 ng/mL) FGF2 concentration. The medium was changed only when the colonies were split, i.e. every 3rd-4th day. Human ESC colonies retained both normal morphology (A) and pluripotency marker expression (Oct4, B), even in the lowered FGF2 concentration.

Due to the instability of wild-type FGF2, every day change of the culture medium is inevitable to maintain pluripotency of human PSC. We therefore tested whether use of thermo-stabilized FGF2 CS2 mutant would bypass this requirement. For that, human ESC were plated on feeder cells in the medium containing standard 4 ng/mL or reduced 1 ng/mL FGF2 mutant, and colonies were grown for following 3-4 days without changing the medium. Results shown in FIG. 12 demonstrate that thermo-stabilized FGF2 CS2 mutant maintains undifferentiated morphology of human ESC as well as expression of pluripotency marker Oct4 even at concentration of 1 ng/mL, and that everyday change of the medium is not required.

Example 11: Repeated Supplementation of the Conditioned Medium is not Required with Thermo-Stabilized FGF2 CS2

Figure 13:
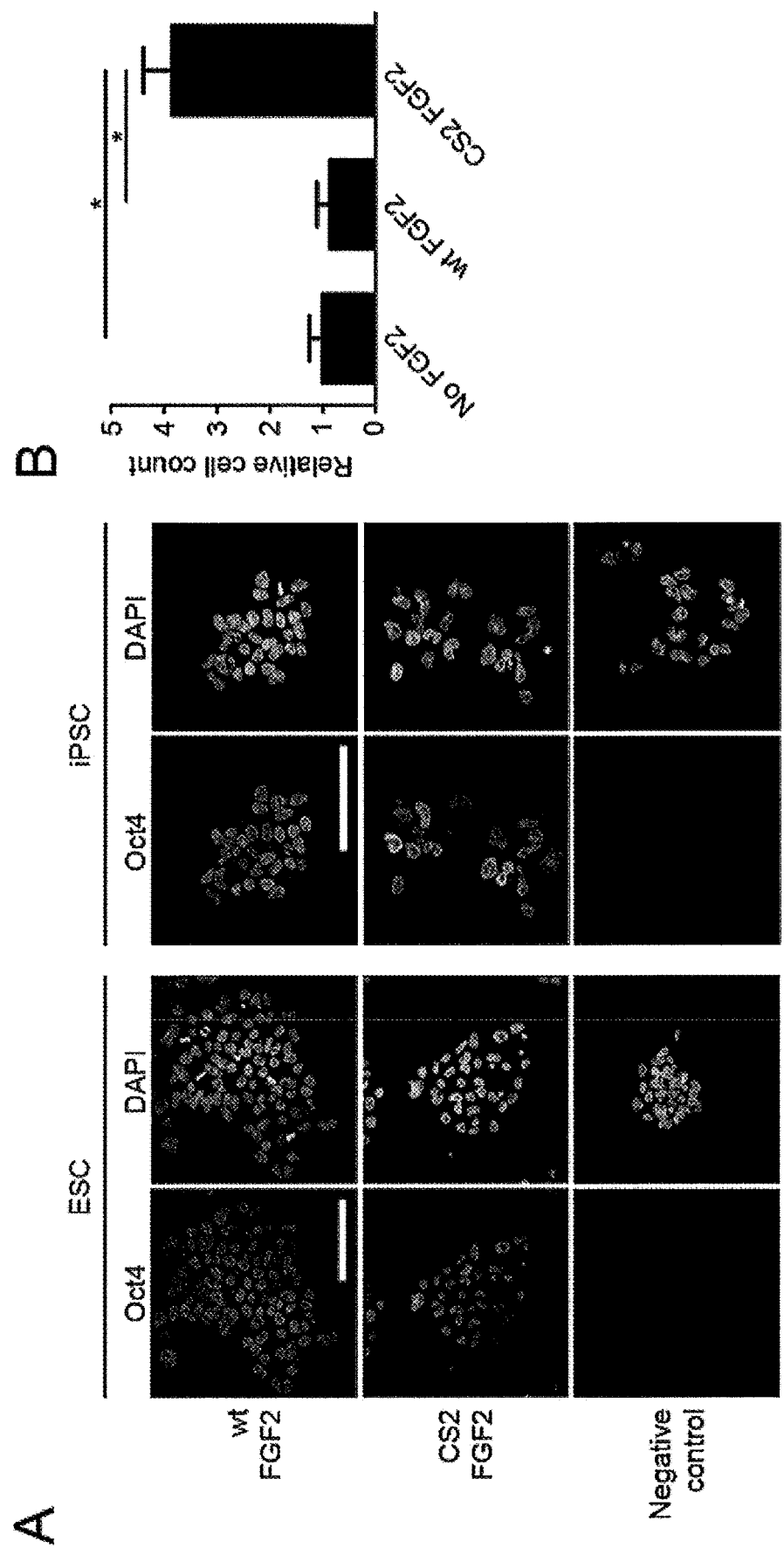
FIG. 13. demonstrates that repeated supplementation of conditioned medium (CM) is not required with FGF2 CS2. To test the long-term stability of FGF2, CM was prepared without additional supplementation after being conditioned by feeder cells. Feeder-free human PSC, both ESC (CCTL14) and iPSC (AM13), were propagated for five passages with each of the tested FGF2, and the expression of pluripotency markers (A) and proliferation (B) was monitored. The expression of Oct4 remains high with both FGF2s (A). Scale bars, 100 μm. FGF2 CS2 shows superior capacity to support proliferation compared to wild type FGF2 (B). Columns show means, error bars show SEM. Student's t-test, *p<0.001, p<0.01, *p<0.05

Because wild-type FGF2 gets inactivated and degraded during preparation of CM, the culture medium needs to be supplemented by FGF2 before and after conditioning by feeder cells. Therefore, we tested the capability of the thermo-stabilized 6-point FGF2 mutant to maintain undifferentiated growth of human PSC without additional supplementation of medium after being conditioned by feeder cells (CM III, FIG. 14). Feeder-free human PSC were propagated for five passages with both wild-type and FGF2 mutant, and the expression of pluripotency markers and proliferation was monitored. While the expression of pluripotency markers remains unaffected (FIG. 13A), the 6-point FGF2 mutant shows superior capacity to support proliferation compared to wild type FGF2 (FIG. 13B).

Example 12: Prediction and Construction of Stable Mutants of FGF2 by Saturation Mutagenesis Positions for saturation mutagenesis that should reveal additional stabilizing mutations were proposed using force-field calculations. Mutations were divided into three groups according to predicted change in Gibbs free energy ($\Delta\Delta G$). Mutations with $\Delta\Delta G < -1.0$ kcal/mol were classified as stabilizing, $1.0 < \Delta\Delta G < -1.0$ as neutral and $\Delta\Delta G > 1.0$ as destabilizing. Eleven positions (K30, E54, E67, C78, R90, S94, C96, E108, N113, T121, and S152) with the highest number of stabilizing and low number of destabilizing mutations were selected for saturation mutagenesis (Table 5).

TABLE 5

Stabilizing and destabilizing mutations at selected positions of FGF2 predicted by energy-based approach.

| | Force-field 1 | | Force-field 2 | |
| --- | --- | --- | --- | --- |
| Position | Number of stabilizing substitutions | Number of destabilizing substitutions | Number of stabilizing substitutions | Number of destabilizing substitutions |
| K30 | 8 | 5 | 0 | 6 |
| E54 | 6 | 3 | 0 | 0 |
| E67 | 5 | 2 | 0 | 1 |
| C78 | 15 | 0 | 3 | 0 |
| R90 | 4 | 2 | 0 | 5 |
| S94 | 5 | 4 | 2 | 1 |
| C96 | 17 | 0 | 0 | 0 |
| E108 | 9 | 2 | 0 | 5 |
| N113 | 13 | 2 | 5 | 4 |
| T121 | 4 | 2 | 2 | 0 |
| S152 | 5 | 2 | 0 | 1 |

All 11 single-site saturation mutagenesis libraries of FGF2 were prepared by gene synthesis. Wild-type Fgf2 cDNA (FIG. 2) fused to the N-terminal sequence containing 6×His tag and thrombin cleavage recognition site subcloned into the pET28b vector was used as a template for mutagenesis. The libraries were constructed using "Fixed Oligo" technology that allows only 20 proteinogenic amino acids to occur in position corresponding to the degenerated codon in nucleotide sequence. Libraries were delivered as lyophilized plasmid DNA. DNA pellets were dissolved in sterile water to the final concentration of 250 ng·$\mu L^{-1}$. Volume of 1 µl from each library was electroporated into 100 µl of freshly prepared *E. coli* XJb (DE3) Autolysis cells. Cells were spread on 11 individual LB agar plates with kanamycin of final concentration 50 µg·$mL^{-1}$ and incubated overnight at 37° C. Single colonies from each of 11 LB agar plates were used for inoculation of individual wells in 1 mL 96 deep-well plates containing 250 µl of LB medium with kanamycin (50 µg·$mL^{-1}$). Plates were incubated overnight at 37° C. with shaking of 200 rpm in high humidity chamber. Expression was induced by addition of fresh LB medium with kanamycin, IPTG and L-arabinose to the final concentration 50 μg·mL$^{-1}$, 0.25 mM and 3 mM, respectively. Plates were incubated overnight at 20° C. with shaking. After 22 hrs, the plates were centrifuged and supernatant was drained. Whole microtiter plates with cell pellets were frozen at −70° C. Then, 100 μl of lysis buffer (20 mM sodium phosphate buffer, 150 mM NaCl, pH 7.0) was added into the each well and plates were incubated for 20 min at 30° C. Cell debris was removed from resulting cell lysates and total soluble protein was determined for each plate using Bradford method. The content of FGF2 in % of the total soluble protein was determined by SDS-PAGE and densitometry. The concentrations of total soluble protein in selected crude extract samples in individual libraries ranged from 0.2 to 0.3 mg·mL$^{-1}$. The content of FGF2 in crude extracts ranged from 5% to 7% of total soluble protein.

Figure 15:
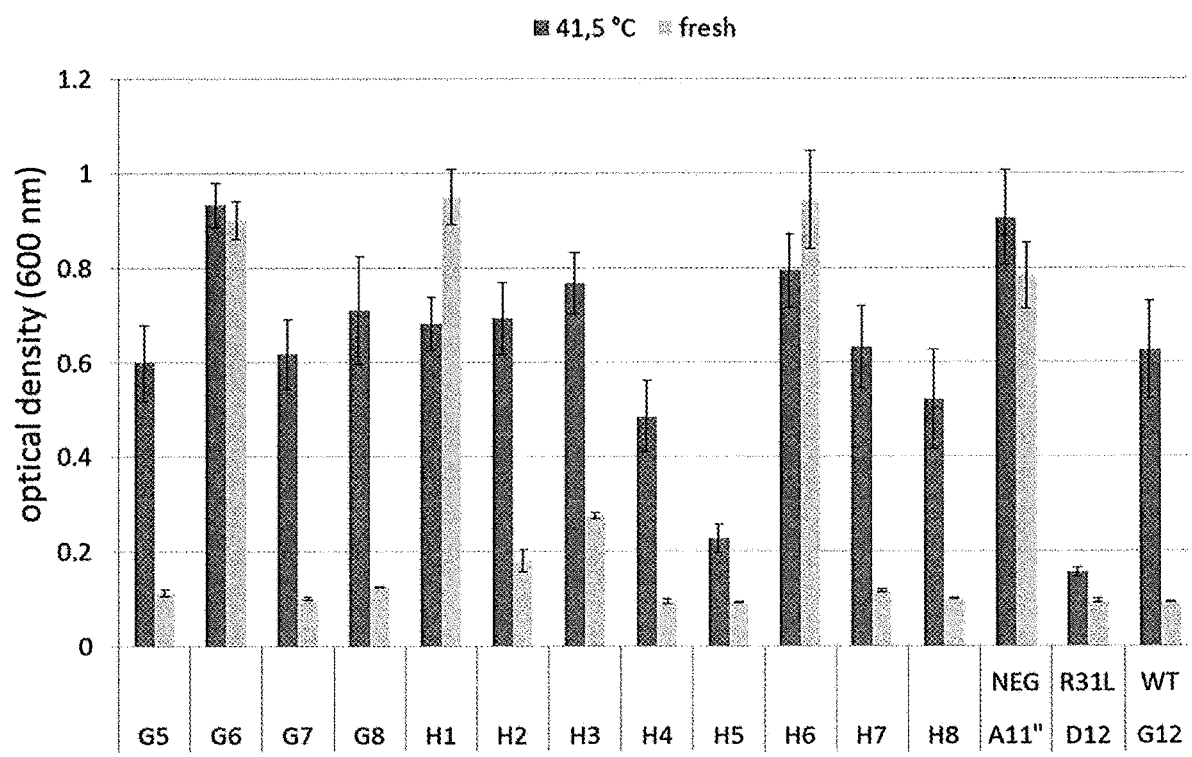
FIG. 15. is an example of output data from screening of biological activity of mutated FGF2 polypeptides in crude extracts (CEs) originating from library FGF2-S152X. Coding on X axis corresponds to the wells of original microtiter plate. FGF2 in freshly melted CEs or CEs preincubated at 41.5° C. was added to the rat chondrocytes grown in parallel microtiter plates to the final concentration of 20 ng·mL$^{-1}$ and inhibition of growth of chondrocytes was compared to the samples containing controls by measuring the optical density of cells. Controls: NEG, negative control (empty plasmid); R31L, positive control (plasmid with single point mutant with improved thermal stability); WT, background control (plasmid with wild-type FGF2). Sample from original clone H5 which shows statistically more significant growth arrest than background control was selected as positive hit.

The biological activity of cell lysates containing individual FGF2 mutants was determined by growth arrest assay using RSC. Microtiter plates with crude extracts containing mutant of FGF2 and controls were melted in room temperature and preincubated at 41.5° C. for 48 hrs. Preincubated crude extracts were added to the chondrocytes grown in fresh microtiter plates to the final concentration of 20 ng·mL$^{-1}$ and inhibition of growth of chondrocytes was compared to the samples containing controls by measuring the optical density of cells (FIG. 15). The more stable mutant of FGF2 was present in added crude extract, the more evident was the growth inhibition. The growth inhibition was determined also for samples not preincubated in increased temperature. Samples causing more significant growth inhibition than samples containing wild type FGF2 were considered as the positive hits. For each of the positive hits, whole screening procedure as described above was repeated. Mutated Fgf2 genes were sequenced by Sanger method. Resulting sequences were aligned with sequence of wild-type FGF2 to verify inserted mutation (Table 6).

TABLE 6

Overview of the outcome from the screening of 11 saturation mutagenesis libraries of FGF2.

| Library | Confirmed hits | Mutations verified by sequencing |
|---|---|---|
| K30X | 2 | K30I, K30R |
| E54X | 2 | E54D, E54A |
| E67X | 5 | E67F, E67V, E67I, E67H, E67W |
| C78X | 1 | C78M |
| R90X | 1 | R90K |
| S94X | 7 | S94V, S94N, S94M, S94R, S94L, S94T, S94I |
| C96X | 3 | C96Q, C96R, C96N |
| E108X | 2 | E108V, E108H |
| N113X | 0 | — |
| T121X | 7 | T121C, T121F, T121P, T121A, T121H, T121R, T121Q, |
| S152X | 2 | S152Q, S152R |

Figure 16:
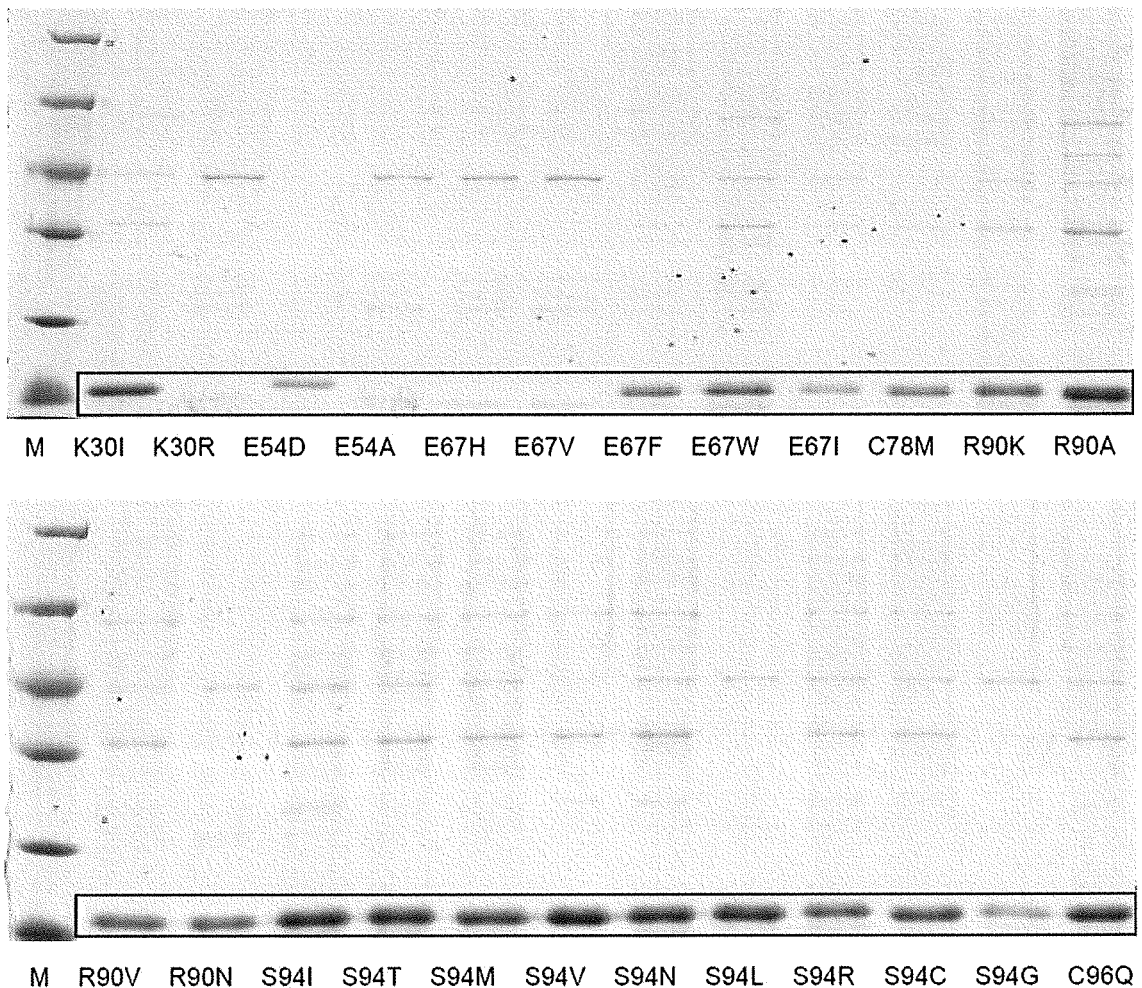
FIG. 16. is SDS-PAGE with samples of FGF2 mutants identified in saturation mutagenesis libraries after purification by MagneHis™ purification system. M, protein marker (116, 66.2, 45, 35, 25, 18.4, 14.4 kDa). App. 19.1 kDa bands of recombinant FGF2 mutants with 6×His tag and thrombin cleavage site are marked by frame.

E. coli BL21(DE3) cells were transformed with expression vectors pET28b-His-thrombin::fgf2x (x=32 different FGF2 mutants), plated on agar plates with kanamycin (50 μg·mL$^{0.1}$) and grown overnight at 37° C. Single colonies were used to inoculate 10 mL of LB medium with kanamycin and cells were grown overnight at 37° C. The expression was induced with IPTG to a final concentration of 0.25 mM. Cells were then cultivated overnight at 20° C. At the end of cultivation, the biomass was centrifuged and the cell pellet was frozen at −70° C. The pellet was defrosted and resuspended in FastBreak™ Cell Lysis Reagent 1×. The lysed cells were incubated for 10-20 minutes at room temperature on a shaking platform. MagneHis™ Ni-Particles were added to cell pellet. To improve binding to MagneHis™ Ni-Particles, 500 mM NaCl was added to the volume bacterial culture (0.03 g NaCl per 1.0 mL of lysate). Tubes containing disrupted bacterial cells were incubated for 2 minutes at room temperature and then placed to the magnetic stand for approximately 30 seconds to capture the MagneHis™ Ni-Particles. The supernatant was carefully removed. To wash out unbound cell proteins, MagneHis™ Binding/Wash Buffer with 500 mM NaCl were added. The supernatant was carefully removed. The wash step was repeated 2 times. The elution of bound proteins was performed by adding 105 μl of MagneHis™ Elution Buffer containing 500 mM NaCl. Elution mixtures were incubated for 2 minutes at room temperature with followed placing tubes in the appropriate magnetic stand for approximately 30 seconds to remove the supernatant containing the purified protein. The presence of all FGF2 mutants was confirmed by SDS-PAGE in 15% polyacrylamide gel (FIG. 16). The yield of purified FGF2 mutant ranges from 10 to 100 mg·L$^{-1}$ while the majority of FGF2 mutants are expressed at similar or higher level than wild type FGF2.

Thermal shift assay was employed for measurement of the thermal stability of target proteins. The measurement was conducted in a 96-microtiter plate. Each well was composed of 2 μL Sypro Orange dye (40× diluted in water) and an appropriate volume of FGF2 mutant calculated using the following equations:

$$VFGF2\ var = (CFGF2\ var * Vdv)/Cdc$$

$$VFGF2\ var = (CFGF2\ var * 1)/2.5$$

where VFGF2 var is volume of FGF2 mutant, CFGF2 var is concentration of FGF2 mutant, Cdc is defined concentration 2.5 mg·mL$^{-1}$, and Vdv is defined as 1 μL. The elution buffer was added last, so that total volume in the well was 25 μL. A thermal-denaturation assay was conducted on real-time PCR system with starting temperature 25° C. ramping up in increments of 1° C. to a final temperature of 95° C. The $T_m$ values were generated by Boltzmann-derived method, where $T_m$ values are taken from the inflection point of the fluorescence melt curve plot (Table 7).

TABLE 7

Thermostability of FGF2 mutants from saturation mutagenesis determined by thermal shift assay. $T_m$ of wild type FGF2 determined by thermal shift assay was 51° C. Amino acid substitutions selected for further computational analysis (see Example 13).

| FGF2 variant | $T_m$ (° C.) | $\Delta T_m$ (° C.) | FGF2 variant | $T_m$ (° C.) | $\Delta T_m$ (° C.) |
|---|---|---|---|---|---|
| K30I | 55 | +4 | S94T | 51 | 0 |
| K3OR | n.d. | — | S94I | 53 | +2 |
| E54D | 53 | +2 | C96Q | 52 | +1 |
| E54A | n.d. | — | C96R | 51 | 0 |
| E67F | 52 | +1 | C96N | 53 | +2 |
| E67V | 52 | +1 | E108V | 49 | −2 |
| E67I | 52 | +1 | E108H | 53 | +2 |
| E67H | n.d. | — | T121C | 50 | −1 |
| E67W | 52 | +1 | T121F | 49 | −2 |
| C78M | 51 | 0 | T121P | 54 | −L-1 |
| R90K | 48 | −3 | T121A | 51 | 0 |
| S94V | 51 | 0 | T121H | 50 | −1 |
| S94N | 50 | −1 | T121R | 50 | −1 |
| S94M | 50 | −1 | T121Q | 52 | +1 |
| S94R | 48 | −3 | S152Q | 49 | −2 |
| S94L | 51 | 0 | S152R | 49 | −2 |

$T_m$: melting temperature; $\Delta T_m$: change in melting temperature upon mutation; n.d., not determined due to the poor protein folding

Example 13: Combination of Single Point-Mutants from Saturation Mutagenesis

Force-field calculations were employed for determination of combinable mutations without antagonistic effect and for the design of multi-site mutants of highly stable FGF2. The following mutations from the library screening (see Example 12) were selected for further analysis: K30I, E54D, S94I, C96N, E108H and T121P. These mutations were combined with existing mutations from FGF2 CS2 mutant (R31L, V52T, H59F, L92Y, C96Y and S109E). All combinations of double-point mutants were constructed in silico to predict additivity of individual mutations. Double-point mutants with the difference between the predicted ΔΔG and the sum of individual single-point mutations >1 kcal·mol$^{-1}$ were considered as antagonistic. Consequently, three different multiple-point mutants were designed for further characterization. All three mutants were based on previously designed FGF2 CS2. FGF2 CS3 mutant (R31L, V52T, H59F, L92Y, C96Y, S109E, K30I, E54D and E108H) contained three additional mutations with the highest stabilizing effects in thermal shift assay. FGF2 CS4 (R31L, V52T, H59F, L92Y, S109E, E54D, S94I, C96N and T121P) was designed with aim to preserve a protein function. All mutations targeting interface between FGF2 and FGFR1 or FGFR2 receptors or positions important for dimerization were discarded, while the mutation C96Y was exchanged for C96N, because of better experimentally verified stabilizing effect. FGF2 CS5 mutant (R31L, V52T, H59F, L92Y, S109E, K30I, E54D, S94I, C96N, E108H and T121P) was selected to maximize the thermostability effect of the protein, containing all mutations found to stabilize FGF2 in the thermal shift assay (Example 12).

Figure 17:
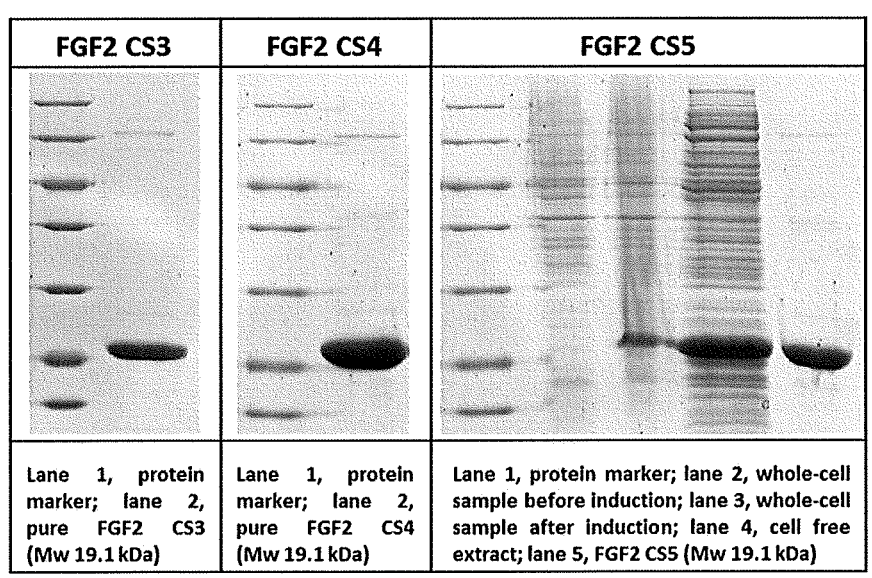
FIG. 17. is SDS-PAGE of purified FGF2 CS3, CS4 and CS5 mutants. Protein marker: 116, 66.2, 45, 35, 25, 18.4, 14.4 kDa. Recombinant FGF2 mutants with 6×His tag and thrombin cleavage site have Mw of app. 19.1 kDa.

Example 14: Construction, Purification and Thermostability Analysis of FGF2 CS3, CS4 and CS5 Mutants Multiple-point mutants of FGF2 were commercially synthesized and subcloned in the NdeI and XhoI sites of pET28b-His-Thrombin downstream inducible T7 promotor (mutated nucleotide and polypeptide sequences are shown in SEQ ID NO:33 to SEQ ID NO:38). Resulting constructs were transformed into *E. coli* Dh5α competent cells. Cells were plated on agar plates with kanamycin (50 μg·mL$^{-1}$) and grown overnight at 37° C. Plasmids were isolated and nucleotide sequences were confirmed by commercial sequencing. *E. coli* BL21(DE3) cells were transformed with expression vectors, plated on agar plates with kanamycin and grown overnight at 37° C. Single colonies were used to inoculate 10 mL of LB medium with kanamycin (50 μg·mL$^{-1}$) and cells were grown overnight at 37° C. Overnight culture was used to inoculate 200 mL of LB medium with kanamycin. Cells were cultivated at 37° C. The expression was induced with IPTG to a final concentration of 0.25 mM. Cells were then cultivated overnight at 20° C. At the end of cultivation, biomass was harvested by centrifugation and washed by buffer (20 mM potassium phosphate buffer, pH 7.5, 0.5 M NaCl, 10 mM imidazole). Cells in suspension were disrupted by sonication and cell lysate was centrifuged. Proteins were purified from crude extracts using single step nickel affinity chromatography. The presence of proteins in peak fractions was proved by SDS-PAGE in 15% polyacrylamide gel (FIG. 17). Precipitation of proteins was minimized by dialysis against buffer containing 750 mM NaCl. The yields of mutants were between 5 and 10 mg/l. DSC was used to characterize protein thermal stability. FGF2 mutants were diluted to 1.0 mg·mL$^{-1}$ for DSC experiments. Data collection was performed over a temperature range of 20° C.-90° C. at the speed of 1° C./min. FGF2 CS3, FGF2 CS4 and FGF2 CS5 mutants exhibited T$_m$ 72.6, 72.2 and 72.7° C., respectively.

Example 15: Proliferation of NIH/3T3 Cells by Thermo-Stabilized FGF2 CS4

Figure 18:
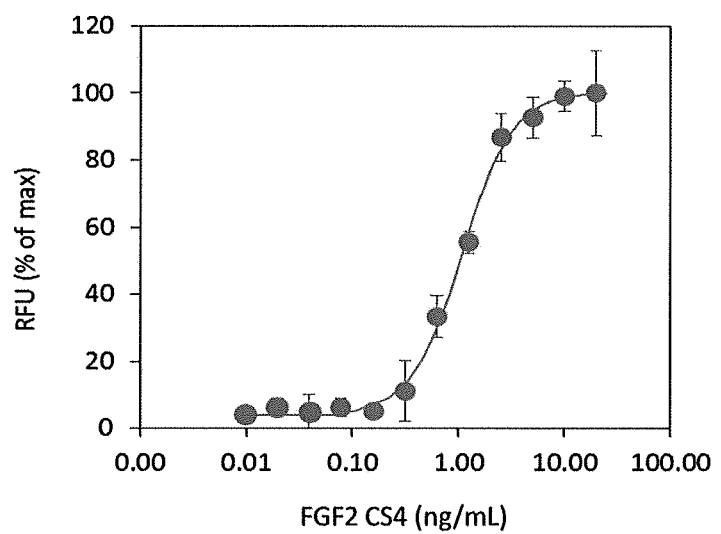
FIG. 18. Proliferation of NIH/3T3 cells induced by FGF2 CS4 recombinant protein.

NIH/3T3 cells were seeded in a density of 40,000 cells/cm2 in 190 μl of medium per well (DMEM 31966, Gibco®+P/S+10% newborn calf serum). After 24 hours, media was changed for starvation (DMEM 31966, Gibco®+P/S+0.5% newborn calf serum). After 16 hours, cells were diluted in sterile water and treated by adding FGF2 CS4 to final concentrations of 0.01-20 ng/mL and the cells were cultured for an additional 48 hours at 37° C. Cell proliferation was measured using CyQuant® fluorescence assay (FIG. 18). Experiments were performed in triplicate. The EC50 for FGF2 CS4, i.e., the concentration of FGF2 CS4 that produces one-half the maximal response, as determined in a proliferation assay of NIH/3T3 cells, is 0.6-1.1 ng/mL.

The invention claimed is:

1. A thermostable polypeptide possessing FGF2 activity and having at least 92% sequence identity to SEQ ID NO: 2, and comprising at least an amino acid substitution R31L.

2. The thermostable polypeptide according to claim 1, wherein the polypeptide has at least 95% sequence identity to SEQ ID NO: 2.

3. The thermostable polypeptide according to claim 1 further comprising at least two amino acid substitutions selected from a group consisting of V52T, H59F, L92Y, C96Y, S109E, K30I, E54D, S94I, C96N, E108H, T121P.

4. The thermostable polypeptide according to claim 3, wherein the polypeptide comprises amino acid substitutions R31L, V52T and H59F.

5. The thermostable polypeptide according to claim 1 further comprising at least five amino acid substitutions selected from a group consisting of V52T, H59F, L92Y, C96Y, S109E, K30I, E54D, S94I, C96N, E108H, T121P.

6. The thermostable polypeptide according to claim 5, wherein the polypeptide comprises amino acid substitutions R31L, V52T, H59F, L92Y, C96Y, S109E.

7. A thermostable polypeptide possessing FGF2 activity, having SEQ ID NO: 2, and comprising at least an amino acid substitution R31L, and comprising at least eight further amino acid substitutions selected from a group consisting of V52T, H59F, L92Y, C96Y, S109E, K30I, E54D, S94I, C96N, E108H, T121P.

8. The thermostable polypeptide according to claim 7, wherein the polypeptide comprises amino acid substitutions K30I, R31L, V52T, E54D, H59F, L92Y, C96Y, E108H, S109E.

9. The thermostable polypeptide according to claim 7, wherein the polypeptide comprises amino acid substitutions R31L, V52T, E54D, H59F, L92Y, S94I, C96N, S109E, T121P.

10. A thermostable polypeptide possessing FGF2 activity, having SEQ ID NO: 2, and comprising at least an amino acid substitution R31L, and comprising at least ten further amino acid substitutions selected from a group consisting of V52T, H59F, L92Y, C96Y, S109E, K30I, E54D, S94I, C96N, E108H, T121P.

11. The thermostable polypeptide according to claim 10, wherein the polypeptide comprises amino acid substitutions K30I, R31L, V52T, E54D, H59F, L92Y, S94I, C96N, E108H, S109E, T121P.

12. A culture medium suitable for culturing human pluripotent stem cells in an undifferentiated state, comprising an effective amount of the thermostable polypeptide defined in any of claim 1, 7, or 10, in the range of 1.0 ng/ml to 100 ng/ml of culture medium.

13. The culture medium according to claim 12 wherein the polypeptide comprises amino acid substitutions defined in claim 4.

14. The culture medium according to claim 12 wherein the polypeptide comprises amino acid substitutions defined in claim 6.

15. The culture medium according to claim 12 wherein the polypeptide comprises amino acid substitutions defined in claim 8.

16. The culture medium according to claim 12 wherein the polypeptide comprises amino acid substitutions defined in claim 9.

17. The culture medium according to claim 12 wherein the polypeptide comprises amino acid substitutions defined in claim 11.

* * * * *

UNITED STATES PATENT AND TRADEMARK OFFICE
CERTIFICATE OF CORRECTION

Page 1 of 2

PATENT NO. : 11,746,135 B2
APPLICATION NO. : 15/778743
DATED : September 5, 2023
INVENTOR(S) : Petr Dvorak et al.

It is certified that error appears in the above-identified patent and that said Letters Patent is hereby corrected as shown below:

On the Title Page

Column 1, Page 2, item (57) Abstract, Lines 2-3, "culturing a human pluripotent stem cells" should be --culturing human pluripotent stem cells--.

Column 1, Page 2, Line 49, "Stabilizign" should be --Stabilizing--.

Column 2, Page 2, Line 10, "visualizaing" should be --visualizing--.

In the Specification

Column 1, Line 12, "culturing a human pluripotent stem cells" should be --culturing human pluripotent stem cells--.

Column 1, Lines 38-39, "culturing a mammalian stem or proginator cells" should be --culturing mammalian stem or proginator cells--.

Column 1, Lines 66-67, "addition of some agents describe" should be --addition of some agents is described in--.

Column 4, Lines 35-39, "culturing a human pluripotent stem cells in a undifferentiated state," should be --culturing human pluripotent stem cells in an undifferentiated state,--.

Column 4, Line 39, "according the invention," should be --according to the invention,--.

Column 4, Line 66, "definition" should be --definitions--.

Column 5, Line 3, "pertain." should be --pertains.--.

Column 6, Line 59-60, "exhibition any of the substitutions" should be --exhibition of any of the Signed and Sealed this
Twenty-eighth Day of November, 2023

Katherine Kelly Vidal
*Director of the United States Patent and Trademark Office*

CERTIFICATE OF CORRECTION (continued)
U.S. Pat. No. 11,746,135 B2 substitutions--.

Column 7, Line 60, "1857)" should be --1857).--.

Column 8, Lines 34-35, "TSA is high-throughput method" should be --TSA is a high-throughput method--.

Column 8, Lines 44-45, "result in a FGF2 mutants" should be --result in FGF2 mutants--.

Column 8, Lines 61-62, "a stable FGF2 polypeptides" should be --stable FGF2 polypeptides--.

Column 19, Line 8, "into the each well" should be --into each well--.